(12) United States Patent
Gaillot et al.

(10) Patent No.: US 10,918,794 B2
(45) Date of Patent: *Feb. 16, 2021

(54) MEDICAL DELIVERY DEVICE

(71) Applicant: HOFFMANN-LA ROCHE INC., Little Falls, NJ (US)

(72) Inventors: Maxime Gaillot, Basel (CH); Roberta Leah, Basel (CH); Declan Reilly, Basel (CH); Mark Digby Teucher, Bath (GB); Paul Graham Hayton, Bristol (GB); Jonathan Paul Ridley, Bristol (GB); James Robert Coop, Bristol (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 273 days.

This patent is subject to a terminal disclaimer.

(21) Appl. No.: 16/062,010

(22) PCT Filed: Dec. 13, 2016

(86) PCT No.: PCT/EP2016/080823
§ 371 (c)(1),
(2) Date: Jun. 13, 2018

(87) PCT Pub. No.: WO2017/102742
PCT Pub. Date: Jun. 22, 2017

(65) Prior Publication Data
US 2018/0369491 A1 Dec. 27, 2018

(30) Foreign Application Priority Data

Dec. 14, 2015 (EP) ..................................... 15199909
Dec. 14, 2015 (EP) ..................................... 15199911
(Continued)

(51) Int. Cl.
*A61M 5/315* (2006.01)
*A61M 5/20* (2006.01)
(Continued)

(52) U.S. Cl.
CPC ................ *A61M 5/204* (2013.01); *A61J 1/20* (2013.01); *A61J 1/2006* (2015.05); *A61J 1/2096* (2013.01);
(Continued)

(58) Field of Classification Search
CPC .............. A61M 5/204; A61M 5/31571; A61M 5/3213; A61M 5/31561; A61M 5/3158;
(Continued)

(56) References Cited

U.S. PATENT DOCUMENTS 4,312,343 A  1/1982 Leveen et al.
4,583,978 A * 4/1986 Porat .................. A61M 5/31511
                                                              604/208
(Continued)

FOREIGN PATENT DOCUMENTS

JP   S56-028770 A   3/1981
JP   2003-527933 A  9/2003
(Continued)

OTHER PUBLICATIONS

International Search Report dated Apr. 18, 2017 in corresponding International Patent Application No. PCT/EP2016/080823.
(Continued)

*Primary Examiner* — Laura A Bouchelle
*Assistant Examiner* — Anh Bui
(74) *Attorney, Agent, or Firm* — Medler Ferro Woodhouse & Mills PLLC; Teresa Medler

(57) ABSTRACT

A medical delivery device is disclosed having a rod element and a dosage member. The rod element has a stem and a first thread arrangement. The dosage member includes a delivery
(Continued)

orifice, a chamber body and a second thread arrangement. The stem of the rod element extends within the chamber body and the delivery orifice is arranged adjacent to a proximal end of the stem. The dosage chamber is formed within the chamber body between the stem and the delivery orifice such that the dosage chamber increases when the rod element moves away from the delivery orifice. In a dosing status, the first thread arrangement of the rod element engages the second thread arrangement of the dosage member such that the rod element is moveable along its longitudinal axis relative to the delivery orifice of the dosage member.

15 Claims, 18 Drawing Sheets

(30) Foreign Application Priority Data

| Dec. 14, 2015 | (EP) | 15199913 |
|---|---|---|
| Dec. 14, 2015 | (EP) | 15199915 |
| May 3, 2016 | (EP) | 16167999 |

(51) Int. Cl.
| | | |
|---|---|---|
| *A61M 5/178* | (2006.01) | |
| *A61J 1/20* | (2006.01) | |
| *A61M 5/32* | (2006.01) | |
| *A61M 5/24* | (2006.01) | |
| *A61M 5/31* | (2006.01) | |

(52) U.S. Cl.
CPC ............ *A61M 5/1782* (2013.01); *A61M 5/20* (2013.01); *A61M 5/2422* (2013.01); *A61M 5/3146* (2013.01); *A61M 5/3158* (2013.01); *A61M 5/31505* (2013.01); *A61M 5/31525* (2013.01); *A61M 5/31528* (2013.01); *A61M 5/31536* (2013.01); *A61M 5/31551* (2013.01); *A61M 5/31553* (2013.01); *A61M 5/31561* (2013.01); *A61M 5/31571* (2013.01); *A61M 5/3213* (2013.01); *A61M 2005/3126* (2013.01); *A61M 2205/58* (2013.01); *A61M 2205/581* (2013.01); *A61M 2205/582* (2013.01); *A61M 2205/583* (2013.01)

(58) Field of Classification Search
CPC ............ A61M 5/31536; A61M 5/20; A61M 5/31551; A61M 5/31505; A61M 5/3146; A61M 5/2422; A61M 5/1782; A61M 5/3153; A61M 5/31528; A61M 5/31525; A61M 2205/58; A61M 2205/582; A61M 2205/581; A61M 2205/583; A61M 2005/3126; A61J 1/2006; A61J 1/2096; A61J 1/20

See application file for complete search history.

(56) References Cited

U.S. PATENT DOCUMENTS

| 4,810,249 A | 3/1989 | Haber et al. | |
|---|---|---|---|
| 6,607,508 B2 | 8/2003 | Knauer | |
| 2001/0037087 A1* | 11/2001 | Knauer | A61M 5/204 604/137 |
| 2003/0105430 A1 | 6/2003 | Lavi et al. | |
| 2011/0034870 A1 | 2/2011 | Glejboel et al. | |

FOREIGN PATENT DOCUMENTS

| JP | 2010-527248 A | 8/2010 | |
|---|---|---|---|
| JP | 2012-528639 A | 11/2012 | |
| JP | 2013-507214 A | 3/2013 | |
| JP | 2014-527894 A | 10/2014 | |
| JP | 2015-526218 A | 9/2015 | |
| JP | 2016-530018 A | 9/2016 | |
| JP | 2018-537209 A | 12/2018 | |
| JP | 2019-502442 A | 1/2019 | |
| WO | 01/52920 A2 | 7/2001 | |
| WO | WO-0152920 A2 * | 7/2001 | A61J 1/2096 |
| WO | 2008/093063 A2 | 8/2008 | |
| WO | 2008/119691 A2 | 10/2008 | |
| WO | 2010/139671 A1 | 12/2010 | |
| WO | 2011/095488 A1 | 8/2011 | |
| WO | 2012/143437 A1 | 10/2012 | |
| WO | 2017/102760 A1 | 6/2017 | |

OTHER PUBLICATIONS

Written Opinion dated Apr. 18, 2017 in corresponding International Patent Application No. PCT/EP2016/080823.
Notice of Reasons for Rejection dated Dec. 1, 2020 in corresponding Japanese Patent Application No 2018-530746.
Search Report dated Nov. 10, 2020 in corresponding Japanese Patent Application No. 2018-530746.
Notice of Reasons for Rejection dated Dec. 1, 2020 in corresponding Japanese Patent Application No. 2018-530680.
Search Report dated Nov. 10, 2020 in corresponding Japanese Patent Application No. 2018-530680.
Notice of Reasons for Rejection dated Dec. 1, 2020 in corresponding Japanese Patent Application No. 2018-530752.
Search Report dated Nov. 10, 2020 in corresponding Japanese Patent Application No. 2018-530752.
Notice of Reasons for Rejection dated Nov. 13, 2020 in corresponding Japanese Patent Application No. 2018-530751.
Search Report dated Nov. 6, 2020 in corresponding Japanese Patent Application No. 2018-530751.

* cited by examiner

MEDICAL DELIVERY DEVICE

TECHNICAL FIELD

The present invention relates to a medical delivery device according to the preamble of independent claim 1. Such a device can be embodied by the following components: (i) a rod element extending into the interior of the housing and having a stem with a longitudinal axis, a first thread arrangement, a distal end and a proximal end; and (ii) a dosage member extending into the interior of the housing and comprising a delivery orifice and a chamber body with a distal end, a proximal end and a hollow interior. The stem of the rod element extends into the interior of the chamber body of the dosage member and the delivery orifice is arranged adjacent to the proximal end of the stem of the rod element. In a dosing status of the medical delivery device, the rod element is movable along its longitudinal axis relative to the delivery orifice of the dosage member by the first thread arrangement of the stem of the rod element and a second thread arrangement travelling along each other. A dosage chamber is formed in the interior of the chamber body of the dosage member between the stem of the rod element and the delivery orifice when the rod element moves away from the delivery orifice. Devices of this kind can be used for a patient self-administering a liquid such as a medicament or a drug.

BACKGROUND ART

Delivering a liquid or other fluid out of a container is required in many medical applications and performed in a plurality of different ways. Particularly where it is essential that the liquid is comparably precisely provided, specific devices are commonly used. For example, liquid pharmaceutical substances are often provided in glass or plastic vials which are closed by a septum or rubber plug and a cap clamped around it or another similar seal cover. Conventionally, for delivering the pharmaceutical substance out of vials, syringes can be used. Thereby, a needle of the syringe penetrates the septum or cover and the pharmaceutical substance is withdrawn into the syringe through its needle. Once transferred into the syringe, the pharmaceutical substance is delivered in an appropriate manner. For example, the pharmaceutical substance can be, e.g. subcutaneously or intramuscularly, injected or it can be orally applied or provided as droplets, e.g., in the eyes or nose of the patient.

Delivering liquids from vials or containers by means of syringes usually is comparably difficult. This typically makes it necessary that an educated person such as a doctor or a nurse is involved. In particular, in cases where the dosage of liquid delivered has to be comparably precise such as when comparable small volumes as in a range of ten microliter to about one milliliter are involved patients are typically not capable of performing the delivery themselves when using a syringe or a similar device, i.e. self-administration can be challenging for the user. However, self-administration of liquids or medicaments is beneficial in many therapeutic applications since the effort for the patient and the costs of the therapy can be extensively reduced.

For improving this situation, there are devices used which allow for more conveniently delivering a comparably precise volume of liquids. For example, it is known to provide medicaments in prefilled syringes which can be administered by the patients themselves. However, such prefilled syringes are often not preferred for plural reasons. For example, producing prefilled syringes is comparably complicated and expensive compared to vials in terms of manufacturing. Or, syringes have to be provided with plural possible dosages suitable for different applications and patients which makes manufacture comparably cumbersome. Other examples of delivery devices are injection pens which are often used in therapy of diabetes.

A further delivery device is described in U.S. Pat. No. 6,607,508 B2, i.e. an automatic medicament delivery device having a cylindrical syringe barrel into which a plunger rod extends from one side. The other side of the syringe barrel is equipped with a thread onto which a needle assembly can be screwed. The plunger rod has a vial seat into which a vial can be retained. The plunger rod is further equipped with a pathway longitudinally extending throughout the entire plunger rod. Radially from the plunger rod pins extend which inter-engage with slots of a dose barrel surrounding the section of the plunger rod having the pins. By turning the dose barrel via a dose ring the plunger rod translates and a volume is created between the plunger rod and the thread side of the syringe barrel. Induced by this movement a medicament is transferred from the vial through the pathway into the volume. The turning of the dose barrel into an opposite direction is blocked by a ratchet mechanism which ensures that no liquid can be pressed back through the pathway. The device further has a spring driven and automatic needle injecting arrangement for delivering the medicament from the volume through a needle screwed to the thread of the syringe barrel. During medicament delivery the plunger rod is automatically turned in the opposite direction by a spring force and the volume is reduced. Thereby, the medicament is pressed through the needle.

Even though such known delivery devices are improving the situation with respect to a convenient handling, they still are comparably complicated to use particularly for precisely dosing and for administering the liquid after dosing. Also, delivery of the liquid can be rather slow which makes the administration comparably cumbersome.

Therefore, there is a need for a medical delivery device allowing on one hand for a precise dosing of a liquid out of a container and on the other hand for a convenient self-administration of the liquid.

DISCLOSURE OF THE INVENTION

According to the invention this need is settled by a medical delivery device as it is defined by the features of independent claim 1. Preferred embodiments are subject of the dependent claims.

In particular, the invention deals with a medical delivery device comprising a rod element and a dosage member. The rod element has a stem with a longitudinal axis, a first thread arrangement, a distal end and a proximal end. The dosage member comprises a second thread arrangement, a delivery orifice and a chamber body with a distal end, a proximal end and a hollow interior. The stem of the rod element extends into the interior of the chamber body. The delivery orifice is arranged adjacent to the proximal end of the stem of the rod element.

In a dosing status of the medical delivery device, the rod element is movable along its longitudinal axis relative to the delivery orifice of the dosage member by the first thread arrangement of the stem of the rod element and the second thread arrangement of the dosage member travelling along each other. Thereby, a dosage chamber is formed in the interior of the chamber body of the dosage member between the stem of the rod element and the delivery orifice which increases when the rod element moves away from the delivery orifice. Further, in the dosing status of the medical delivery device, the first thread arrangement of the rod element engages the second thread arrangement of the dosage member.

The term "proximal" as used in connection with the invention and disclosed embodiments of medical delivery devices can relate to an orientation of the medical delivery device which in its intended use is directed to a body of the patient. Thereby, proximal portions or parts can be directed to or positioned closer to the body of the patient when the medical delivery device is applied to the patient. Contrary, the term "distal" as used in connection with the invention and the disclosed embodiments of medical delivery devices can relate to an orientation of the medical delivery device which in its intended use is directed away from the body of the patient. For example, in a conventional syringe the proximal end usually is the tip of the needle and the distal end is the end of the plunger where the thumb is to be pushed.

The first thread arrangement can be an inner thread arrangement and, correspondingly, the second thread arrangement can be an outer thread arrangement. The term "outer" in connection with the thread arrangement can relate to a direction into which the thread arrangement is oriented. In particular, it can relate to a thread arrangement being outwardly oriented such that it can interact with a corresponding inner thread arrangement. Similarly, the term "inner" in connection with the thread arrangement can relate to an opposite direction into which the thread arrangement is oriented.

The term "thread" as used herein relates to a male structure such as a ridge or a female structure such as a groove extending along and around a surface or body. Typically threads are helically or essentially helically shaped and run along and around a body or part.

Within the medical delivery device according to the invention and the disclosed embodiments of medical delivery devices rotating the dosage member and the rod element relative to each other can be embodied by either the dosage member rotating around the rod element, the rod element rotating in or around the dosage member or the dosage member and the rod element both rotating. For an efficient appropriate rotational movement the dosage member and the rod element can be coaxially arranged.

The term "travel along each other" as used in connection with the first and second thread arrangements can relate to a part being moved or shifted in or on the thread. For example, a male member such as a pin can be moved in and along a groove of a female thread.

The stem of the rod element and of rod elements of the disclosed embodiments of medical delivery devices can have the shape of a post or cylinder. While extending into the interior of the chamber body of the dosage member the distal end of the body of the rod element can lie close to the distal end of the chamber body and the proximal end of the stem of the rod element can lie close to the proximal end of the chamber body.

The delivery orifice and delivery orifices of the disclosed embodiments of medical delivery devices can be shaped for a particular application or administration of a medicament or drug to be delivered by the device. For example, it can be a needle if the device is intended for injecting a medicament. In such an embodiment the needle can extend from the interior of a housing as described below through its proximal opening out of the housing or a specific part thereof. The delivery orifice can also be adapted for being connected to a delivery member. For example, it can comprise a male or female part of a Luer lock or Luer taper connector and the delivery member can be equipped with a corresponding female or male Luer lock connector. The delivery orifice can be arranged at the proximal end of the dosage member.

The medical delivery device according to the invention and the enclosed embodiments of medical delivery devices can be made of a plastic material. In particular, it can be made of a sterilisable plastic material which can be manufactured in an injection molding process.

Since in accordance with the invention the dosage member directly comprises the second thread arrangement a robust and efficient implementation of the medical delivery device being suitable for various therapeutic application can be achieved. It can be prevented that a large number of parts has to be embodied for the dosing. Furthermore, the first thread arrangement of the rod element engaging the second thread arrangement of the dosage member, in the dosing status of the medical delivery device allows for precisely dosing a liquid particularly also at comparably small volumes such as between 10 µl and 1 ml. Thus, the medical delivery device allows on one hand to precisely dosing a liquid, for example from a container, and on the other hand for a convenient self-administration of the liquid after being dosed.

Preferably, the medical delivery device comprises a housing having an interior, a proximal opening and a distal opening, wherein the rod element extends into the interior of the housing and the dosage member extends into the interior of the housing. The delivery orifice can extend from the interior of the housing through its proximal opening out of the housing.

The housing can be more or less cylindrically shaped. The distal and proximal openings can be embodied at respective distal and proximal end sides of the housing. It can have a flange portion as finger rest at or near its distal end in which the distal opening is arranged. The housing can particularly form an outer envelope of the medical delivery device. It can be shaped to allow a convenient handling and use of the device as well as to protect the components in its interior.

The term "extend into" as used herein in connection with the rod element, the dosage member, the housing or another part can relate to being fully or partially arranged inside. It can, for example, relate to an arrangement where a portion of a part is partially outside another part but projects into the other part.

Preferably, the second thread arrangement is arranged at an outer surface of the chamber body of the dosage member, the first thread arrangement of the rod element comprises an arm section extending beneath the stem and, in the dosage status of the delivery device, the first thread arrangement of the rod element engages the second thread arrangement of the dosage member via the arm section. The arm section can comprise plural arms such as, e.g., two arms or the like.

The first thread arrangement of the stem of the rod element and the second thread arrangement of the dosage member can comprise a thread and a male member.

Thereby, in the dosing status, the male member can travel along the thread when turning the dosage member in relation to the stem of the rod element. The thread can be embodied as an inner thread on the dosage member and the second thread arrangement can comprise a male member such as a pin extending into the inner thread. Preferably, the first thread arrangement of the rod element is a pin arrangement with at least one pin as a male member, the second thread arrangement of the dosage member comprises a thread and the first thread arrangement of the rod element engages the second thread arrangement of the dosage member by the at least one pin of the pin arrangement of the rod element being located in the thread of the second thread arrangement of the dosage member. Thereby, the pin arrangement can be a male inner thread arrangement and the thread a female outer thread arrangement.

Preferably, in the dosing status of the medical delivery device, the dosage member is rotatable in relation to the rod element such that the first thread arrangement of the rod element and the second thread arrangement of the dosage member travels along each other and the rod element moves along the longitudinal axis of its stem relative to the delivery orifice. This allows for an efficient dosing involving a comparably simple set up. Thereby, the medical delivery device preferably comprises a dosing activator, wherein the dosage member has a first coupling structure, the dosing activator has a second coupling structure corresponding to the first coupling structure and the dosing activator is torque resistantly connected to the dosage member when the second coupling structure is mounted to the first coupling structure. Such a dosing activator may allow for an accurate dosing with the medical delivery device. It can, e.g., be removed before delivery.

In particular, the dosing activator can be mounted to the dosage member in the dosing status of the medical delivery device. The first coupling structure can project through the proximal opening of the housing. The dosing activator and the dosage member can be axially aligned which can ease the rotational movement.

The dosing activator preferably comprises a dial unit which is torque resistantly connected to the dosage member when the second coupling structure is mounted to the first coupling structure such that rotating the dial unit rotates the dosage member. Such a dial unit can be embodied with means for convenient dosing operation. For example, it can be equipped with a gripping structure, such as ribs, allowing a comfortable manual operation.

Further, the dosing activator preferably comprises a container seat for holding a container in a predefined position. The term "container" as used herein can relate to any liquid reservoir suitable for storing and transporting a liquid. Where the liquids are medicaments or the like, the container can particularly be a vial. The term "vial" as used in this connection can relate a comparably small vessel or bottle, commonly used to store pharmaceutical products or pharmaceuticals or medicaments in liquid, powdered or capsuled form. The vial can be made of a sterilisable material such as glass or plastic such as, e.g., polypropylene. The container can also comprise plural sub-containers such as plural vials. The term "predefined position" in this context can be such that an opening of the container is oriented towards the delivery orifice. Such a container seat allows for connecting a container at a well predefined position and orientation. This allows for efficiently coupling a container to the system or medical delivery device.

Thereby, the delivery orifice preferably connects the container seat of the dosing activator with the dosage chamber of the dosage member such that, when a container is arranged in the container seat of the dosing activator, an open duct is formed between an interior of the container and the dosage chamber of the dosage member. The open duct allows for transferring a liquid from the container into the dosage chamber when the dosing activator is rotated around the longitudinal axis. More specifically, by rotating the dosing activator the rod element is moved along the longitudinal axis such that the dosage chamber is enlarged or reduced and liquid is transferred from the container into the dosage chamber or vice versa.

The container seat of the dosing activator preferably comprises a spike which penetrates a cap of an opening of a container when the container is arranged in the container seat of the dosing activator. Often, containers are closed by a penetrable cover such as a septum or the like. By having such a spike it can be prevented that the delivery orifice itself has to penetrate the cap. This allows reducing the risk of harming or contaminating the delivery orifice. For example, when the cap comprises a septum and the delivery orifice has a needle, it can be prevented that the needle has to be pierced through the septum which typically contaminates the needle. Thus, the spike allows keeping the delivery orifice in a condition ready for administration such as for injection or the like.

The dosing activator preferably comprises an orifice seal, wherein the orifice seal of the dosing activator seals the delivery orifice of the dosage member when the second coupling structure of the dosing activator is mounted to the first coupling structure of the dosage member. Such an arrangement allows for minimizing a residual volume. Advantageously, the orifice seal is located as close to a tip or proximal end of the delivery orifice as possible. The orifice seal can be shaped as a plug which forms a passage such as a hole or thinner part when the delivery orifice is inserted. It can be made of a plastic material such as a silicone or the like. By means of the orifice seal it can be achieved that the delivery orifice is protected. In particular, it allows to prevent that the delivery orifice is contaminated or the like. Also, the orifice seal can prevent spillage of the drug when the dosing activator is not attached to the drug delivery device. Furthermore, the free space containing air around the delivery orifice can be minimized by the orifice seal. Like this, the amount of air withdrawn together with the content of the container and transferred into the dosage chamber is reduced or even at least essentially eliminated.

Preferably, a fluid is transferred from the container through the delivery orifice to the dosage chamber when the container is arranged in the container seat of the dosing activator and the rod element and the dosage member are rotated in a first direction relative to each other. This allows for an efficient design of the delivery device and for a comfortable dosing. Thereby, the fluid preferably is transferred from the dosage chamber through the delivery orifice to the container when the container is arranged in the container seat of the dosing activator and the rod element and the dosage member are rotated in a second direction opposite to the first direction relative to each other. This permits dosing revision. The dosage in the dosing chamber can, thus, conveniently be varied, adjusted and corrected back and forth until a precise amount of liquid is selected. After switching the medical delivery device to the delivery status or mode further dosing is not possible.

The first thread arrangement of the stem of the rod element and/or the second thread arrangement of the dosage member can be equipped with a plurality of irregularities being positioned in a fixed distance to each other such that, when the first thread arrangement of the stem of the rod element and a second thread arrangement of the dosage member travel along each other, the first thread arrangement of the stem of the rod element and the second thread arrangement of the dosage member interact with one of the plurality of irregularities at a predefined rotating angle. The irregularities can induce an audible and/or tactile signal each time the first thread arrangement and the second thread arrangement pass by a certain rotation. The irregularities can, e.g., be gaps in the walls of the thread.

Thereby, the irregularities can be located such that rotating the dosage member about the predefined rotating angle causes the dosage chamber to change by a predefined volume. Particularly, each rotation about the predefined angle can change the volume of the dosage chamber by the same predefined amount. Like this, a signal can be provided to a user of the medical delivery device during dosing indicating that the dosage volume has been changed by the predefined amount.

Preferably, the medical delivery device comprises a switching mechanism for changing the medical delivery device from the dosing status to a delivery status, wherein in the dosing status of the medical delivery device, moving the rod element along its longitudinal axis by applying an axial force to the rod element is prevented, and in the delivery status of the medical delivery device, the rod element is movable along its longitudinal axis relative to the delivery orifice by applying an axial force to the rod element, and moving the rod element along its longitudinal axis by rotating the dial shell around the stem of the rod element is prevented.

The term "axial force" as used in connection with moving the rod element, when the medical delivery device is in the delivery status, can relate to a force applied to the rod element in order to axially move it. Typically such axial force can be manually induced, e.g. by pushing with a thumb on the distal end of the rod element or on a part mounted to the rod element.

In this connection the term "prevent" can relate to impeding the axial force to axially move the rod element. It is understood that if the axial force is high enough the rod element could still be axially moved, e.g., by breaking or deforming certain parts or features of the device even if axial movement by an axial force is prevented. Thus, preventing the axial movement by an axial force can relate to a proper use of the device.

The switching mechanism can comprise the dosing activator. In particular, the medical delivery device can be designed such that it is in the dosing status, when the dosing activator is mounted to the dosage member and it can only be switched into the delivery status when the dosing activator is removed from the dosage member.

By providing the medical delivery device with the switching mechanism or structure, in use, it can be clearly distinguished between the dosing status and the delivery status. This allows for functionally separating the dosing of a liquid such as a medicament from the delivery of the liquid. Typically, in a first step the medical delivery device is in the dosing status. In this status, the liquid can be precisely dosed into the dosage chamber. Any unintended activation of the medical delivery device, e.g. by applying an axial force to the rod element, which would impair the accuracy of the dosing can be prevented. This makes a precise and safe dosing of the liquid conveniently possible and assures that the liquid is not administered until the dosing selection is finished.

After switching the medical delivery device into the delivery status, further dosing amendments can be prevented which allows for hindering an impairing of the precise dosing during delivery of the liquid. Also, in the delivery status, activation of the medical delivery device can be particularly convenient since no further dosing is possible and accordingly no measures have to be taken to prevent unintendedly changing dosage during administration. This makes self-administration of the liquid particularly convenient and safe. The switching mechanism can be embodied so that it is not possible to switch the medical delivery device back to the dosing status once it is in the delivery status.

Preferably, the switching mechanism comprises a disengaging or mechanical structure which disengages the first thread arrangement of the stem of the rod element from the second thread arrangement of the dosage member upon changing the medical delivery device from the dosing status to the delivery status. By disengaging the first thread arrangement from the second thread arrangement it can be achieved that the rod element is axially moved without being rotated around its longitudinal axis. Thus, the rod element can be transferred by an axial force without any rotational movement. In the meantime, forwarding the stem by a rotational movement can be prevented since the first and second thread arrangement do no longer inter-engage.

Preferably, the switching mechanism comprises a release shell with a recess, wherein in the dosing status of the delivery device, the release shell holds the arm section of the rod element in a constrained position such that the first thread arrangement of the rod element engages the second thread arrangement of the dosage member via the arm section, upon switching the delivery device from the dosing status to the delivery status, the release shell of the switching mechanism is moved relative to the arm section of the rod element, and in the delivery status of the delivery device, the arm section of the rod element is positioned in the recess of the release shell such that the first thread arrangement of the rod element is disengaged from the second thread arrangement of the dosage member.

In embodiments of the arm sections of the rod element having plural arms the release shell can be equipped by corresponding plural recesses. The release shell can have a hollow cylindrical body in which the recess is provided as opening in the cylinder wall. In order to be movable in relation to the rod element, the release shell can be rotatable around the rod element. Thereby, it can for example be rotatable about the longitudinal axis of the stem of the rod element. The release shell together with the constrained arm section allow for efficiently disengaging the first thread arrangement from the second thread arrangement upon a switching the medical delivery device from the dose status to the delivery status. In particular such arrangement allows for an efficient and comparably simple mechanical implementation of the switching mechanism.

Preferably, the rod element comprises a stopper at its proximal end side. In particular, the stopper can be located at a proximal end side of the stem of the rod element. The term "stopper" in this context can relate to a stopper in the narrow sense, i.e. a plug-like sealing member. It can also relate to alternative sealing members such as O-rings mounted to the stem or the like. The stopper can be made of an elastic material such as a rubber in order to comply providing tightness. By means of the stopper the rod element can tightly be arranged in the dosage chamber of the dosage member. Like this, an underpressure, partial vacuum or vacuum can be induced in the dosage chamber which allows for withdrawing liquid into the dosage chamber.

Preferably, the medical delivery device comprises a counter coupled to the rod element such that the counter indicates the dosage volume formed by the rod element when being moved along its longitudinal axis relative to the delivery orifice by rotating the dosage member and the rod element relative to each other. By coupling the counter to the rod element a movement of the latter in relation to the delivery orifice can be identified and directly reflected by adjusting the displayed dosage volume. Like this an efficient implementation of a precise and purely mechanical dosage counter is possible.

Thereby, the counter can remain coupled to second thread arrangement of the dosage member. The dosage member can no longer rotate and longitudinally slides together with the rod element when an axial force is applied.

In operation or usage of medical delivery devices as described above as well as in other medical delivery devices a substantial underpressure is induced in the dosing chamber in order to withdraw a fluid from the container. In particular, during dosing the stem together with a stopper proximally mounted to it is moved away from the delivery orifice. Thereby, the underpressure is generated which in turn sucks the fluid out of the container. Such underpressure may deform the stopper to a certain extent which can impair the dosing accuracy particularly when a comparably high precision is to be achieved or comparably small volumes are to be dosed. Thus, there is a need for a delivery device allowing for a particular precise dosing.

This need is settled by another further aspect of the present disclosure which deals with a medical delivery device comprising a rod element and a dosage member. The rod element has a stem with a longitudinal axis, a distal end, a proximal end and a stopper mounted to a head portion of the proximal end of the stem. The dosage member comprises a delivery orifice and a chamber body with a distal end, a proximal end and a hollow interior, wherein the stem of the rod element extends into the interior of the chamber body of the dosage member the delivery orifice is arranged adjacent to the stopper of the rod element and the stopper tightly fits into the interior of the chamber body.

Particularly, the head portion of the stem of the rod element of the medical delivery device of the other further aspect of the present disclosure has plural bulges and the stopper has a corresponding interior, wherein the complete head portion of the stem is fitted into the interior of the stopper. By providing such bulges to the stem and by appropriately shaping the stopper a deformation of the stopper can be hindered or eliminated. Thus, an increased dosing accuracy can be achieved.

Preferably, in a dosing status of the medical delivery device of the medical delivery device of the other further aspect of the present disclosure, the rod element is movable along its longitudinal axis relative to the delivery orifice of the dosage member, such that a dosage chamber is formed in the interior of the chamber body of the dosage member between the stem of the rod element and the delivery orifice which dosage chamber increases when the rod element moves away from the delivery orifice.

The stopper preferably is made of an elastic or elastomeric material such a rubber or the like.

Preferably, the plural bulges of the head portion of the stem are convex. Such convex bulges may be forced into the stopper which increases retention of the stopper on the stem. Neighbouring of the plural bulges of the head portion of the stem of the rod element preferably are separated by a concave intermediate section. Such a concave section may additionally assist retention of the stopper on the stem.

Preferably, the stem of the rod element comprises an abutting face from which the head portion extends. Thereby, the stopper preferably axially abuts the abutting face of the stem of the rod element. Like this, the stopper can be clamped in between the bulges and abutting face such that it can be precisely positioned.

Preferably, the head portion of the stem of the rod element has a reduced diameter compared to the rest of the stem. Like this, a comparable bulky stopper can be implemented without increasing the maximum diameter of the stem including the stopper.

Preferably, the stem of the rod element is rotational symmetric. In particular, the also the head portion forming part of the stem is rotational symmetric. Thereby, it the stem can be rotational symmetric about it longitudinal axis along which it also is movable. Such a shape of the stem can be efficiently manufactured.

In the medical delivery device according to the invention and in all aspects of the present disclosure described above and below the medical delivery device preferably comprises a cage body, a spring element and a release mechanism, wherein the release mechanism activates the spring element when the rod element is moved along its longitudinal axis relative to the delivery orifice and the dosage chamber is minimized, such that the cage body is moved relative to the delivery orifice thereby covering the delivery orifice.

The term "minimized dosage chamber" in this connection can particularly relate to the dosage chamber being more or less completely emptied. Thereby, the dosage chamber can be essentially eliminated by forwarding the rod element towards the delivery orifice. Such an arrangement allows for efficiently protecting the delivery orifice after delivery. This can be particularly important when the delivery orifice is a needle or a needle like arrangement.

In a possible embodiment the cage body is the housing of the medical delivery device. Like this, after delivery of the dosage the spring element moves the housing relative to the delivery orifice and thereby protects or covers the delivery orifice. In other words the delivery orifice or needle is retracted into the housing by means of the spring element.

Preferably, the release mechanism comprises a lockout member and the spring element is arranged in between the cage body and the lockout member. Such a lockout member allows for distinguishing the spring element from any rotational movement during use of the device (e.g., dosing, delivery, etc.). Like this the dosing and the dosing indication accuracy can be comparably high (i.e., same dosing indication prior and after delivery). In particular, it can be prevented that during dosing any disturbance occurs due to a rotation of the spring element.

Thereby, in the dosing status of the medical delivery device, the lockout member and the cage body preferably are arranged not to be rotated when the first thread arrangement of the rod element and the second thread arrangement travel along each other. Also, preferably, in the dosing status of the medical delivery device, upon the switching mechanism rotating the release shell of the medical delivery device is switched from the dosing status to the delivery status, the release mechanism is prepared to be activated at the end of the delivery process. This arrangement allows for efficiently separating the spring element from any rotational movement during dosing.

Preferably the dosage member and the release mechanism interact such that, when the dosage member is rotated along the longitudinal axis, an appreciable click is produced. The term "appreciable click" in this connection can relate to a hearable sound and/or a sensible signal. It can particularly be produced by the dosage member and the release mechanism engaging.

In operation or usage of medical delivery devices as described above as well as in other medical delivery devices and, more generally, in any application where a typically liquid substance is to be withdrawn from a container closed by a septum or the like usually a needle of the syringe penetrates the septum or cover of the container or vial and the substance is withdrawn into the syringe through its needle. Once transferred into the syringe, the substance is delivered in an appropriate manner. For example, the substance can be a pharmaceutical substance which can be, e.g. subcutaneously or intramuscularly, injected via the needle or which can be orally applied or provided as droplets, e.g., in the eyes or nose of the patient.

When penetrating the septum or cover of the container the needles of syringes often get contaminated by the septum. However, such contaminations are undesired in many applications such as, e.g., when injections are involved. Furthermore, particularly when the syringe is a specific device such as an injection device, often a considerable amount of air is withdrawn into the syringe before the liquid substance. Such air in the syringe typically has to be eliminated out of the syringe before applying the substance in a priming step. Priming steps can make it difficult to dose and deliver a precise amount of liquid particularly when the amount of liquid is comparably small such as in a range of about 10 µl to 1 ml.

Therefore, there is a need for a device or process allowing for delivering a precise dosage of a liquid in an immaculate condition. This need is settled by another further aspect of the present disclosure which deals with an adapter for connecting a container to a delivery device having a delivery orifice. The adapter comprises a mounting structure arranged to connect the adapter to and disconnect the adapter from the delivery device, and a container seat for holding a container in a predefined position relative to a tip of the delivery orifice. When a container is arranged in the container seat of the adapter and the mounting structure of the adapter is connected to the delivery device, an open duct is formed between an interior of the container and an interior of the delivery orifice of the delivery device. The container seat of the adapter comprises a spike which penetrates a cap of an opening of a container when the container is arranged in the container seat of the dosing activator.

The delivery device can be a device for administering a liquid substance. For example it can be a drug delivery device for applying a liquid medicament. With such delivery devices the liquid substance such as a medicament can be delivered or administered in an appropriate form such as by droplets for the eye, by oral dosages or the like. In particular, the delivery device can be an injection device for subcutaneously or intramuscularly injecting the substance.

The delivery orifice of the adapter can be shaped for a particular application or administration of a medicament to be delivered from the delivery device. It can be a needle if, for example, the delivery device is intended for injecting the medicament. In such an embodiment the delivery orifice or needle can extend from the interior of a housing through its proximal opening out of the housing or a specific part thereof. The delivery orifice can also be adapted for being connected to a delivery member. For example, it can comprise a male or female part of a Luer lock or Luer taper connector and the delivery member can be equipped with a corresponding female or male Luer lock connector. Other examples of delivery orifices are nozzles, valves, fluid guides or the like.

The container can be a container as described above and below. The container seat allows for connecting the container at a well predefined position and orientation. The term "predefined position" in the context of the container seat can be such that an opening of the container is oriented towards the delivery orifice. This allows for efficiently coupling a container to the system or medical delivery device.

The cap of the container can comprise a septum or an elastic stopper. Typically, such septum or stoppers are arranged in an opening of the container for sealing it. The cap can further comprise a metal or plastic cover which is arranged or crimped around the opening and the septum or stopper. The cover can hold and protect the septum or stopper.

The adapter can be made of a plastic material. In particular, it can be made of a sterilisable plastic material which can be manufactured in an injection molding process. It can be essentially cylindrically shaped. Also, it can be part of or integrated in another device such as a dosage activator as described in more detail below. The delivery device or drug delivery device can be a needle device such as a syringe or another injection device.

The open duct allows for transferring a liquid from the container into a dosage chamber of the delivery device when the adapter is mounted to the delivery device and the container is arranged in the container seat. With the adapter it can by means of the spike be prevented that the delivery orifice itself has to penetrate the cap. This allows for reducing the risk of harming or contaminating the delivery orifice of the delivery device. For example, when the cap comprises a septum, it can be prevented that the delivery orifice has to be pierced through the septum which typically contaminates or desiliconizes the delivery orifice and which also can damage the delivery orifice or its tip. Thus, the spike allows keeping the delivery orifice in a condition ready for administration such as for injection or the like. Like this, the adapter allows for delivering a precise dosage of a liquid in an immaculate condition.

Preferably, the spike extends in the interior of the container seat. Such an arrangement of the spike allows for directly penetrating the cap of the container when it is arranged or placed in the container seat. Thereby it can be advantageous when the container seat is adapted for holding the container with its opening directed towards the spike.

Preferably, the spike comprises a tip. The tip can be embodied sharp enough to pierce and penetrate the cap or its septum or stopper. Such a spike allows for conveniently penetrating the cap in an appropriate way. Thereby, the spike preferably comprises a conduit which runs from the tip longitudinally through the spike. The term "longitudinal" in this connection can relate to a direction of the spike. In particular, the spike can be oriented along an axis of the container. The conduit of the spike allows for connecting the container to the delivery orifice and to transfer a liquid from the container to the delivery orifice or dosage chamber.

Preferably, the adapter further comprises a delivery orifice seal which seals the delivery orifice of the delivery device when the mounting structure of the adapter is connected to the delivery device. Such an arrangement allows for minimizing an air volume around the delivery orifice and particularly around its tip. Advantageously, the orifice seal is located as close to the tip or proximal end of the delivery orifice as possible. By means of the orifice seal it can be achieved that the delivery orifice is protected and contamination is reduced. Furthermore, the free space containing air around the delivery orifice or its tip can be minimized by the delivery orifice seal. Like this, the amount of air withdrawn together with the liquid of the container and transferred by the delivery orifice can be reduced or even at least essentially eliminated. Also, the orifice seal can prevent spillage of the drug when the adaptor is not attached to the delivery device.

The adapter further preferably comprises a seal holder in which the delivery orifice seal is tightly arranged. For example, such a seal holder can be embodied as a recess which fits the delivery orifice seal. The delivery orifice seal can then be slightly compressed and pushed inside the recess such that it is held by friction in the recess. The delivery orifice seal preferably is shaped as a plug.

The delivery orifice seal preferably comprises a passage through which the delivery orifice extends when the mounting structure of the adapter is connected to the delivery device. In the passage the delivery orifice can be tightly received. For this, a diameter of the passage can be slightly smaller than of the delivery orifice such that when the delivery orifice is arranged in the passage the delivery orifice seal is lightly deformed which tightens the delivery orifice in the delivery orifice seal.

Preferably, the delivery orifice of the delivery device extends into the conduit of the spike when the mounting structure of the adapter is connected to the delivery device. Like this, the delivery orifice can be arranged comparably close to the spike which allows for minimizing the air volume around the delivery orifice and particularly around its tip. Thus, it can be achieved that comparably few air is withdrawn by the delivery orifice when transferring the liquid from the container into the delivery orifice or dosage chamber.

Thereby, the delivery orifice seal preferably tightly abuts the spike at a side of the spike where the conduit ends opposite to the tip. This allows to further minimizing the free space around the delivery orifice tip such that the amount of air around the tip of the delivery orifice can be minimal.

Preferably, the delivery orifice seal is made of silicone. It can also be made of a plastic material wherein silicone can be particularly beneficial. More specifically, when using silicone in the delivery orifice seal a contamination of the delivery orifice by the delivery orifice seal can be prevented. Also silicone has a sufficient elasticity to be tightly arranged inside the seal holder and to tightly receive the delivery orifice in the conduit.

In the context of the adapter a method of delivering a liquid to a patient comprises the following steps: obtaining a liquid in a container, a delivery device with a delivery orifice and an adapter according to any one of the preceding claims; arranging the container in a container seat of the adapter; withdrawing a liquid from the container into the delivery device via its delivery orifice while the mounting structure of the adapter is connected to the delivery device and the container is arranged in the container seat of the adapter; decoupling the adapter from the delivery device; and optionally providing the liquid out of the delivery device via the delivery orifice. The steps of the method can also be embodied in another sequence than the one listed hereinbefore.

The method according to the invention allows for efficiently achieving the benefits described in connection with the adapter above.

BRIEF DESCRIPTION OF THE DRAWINGS

The medical delivery device according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "proximal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
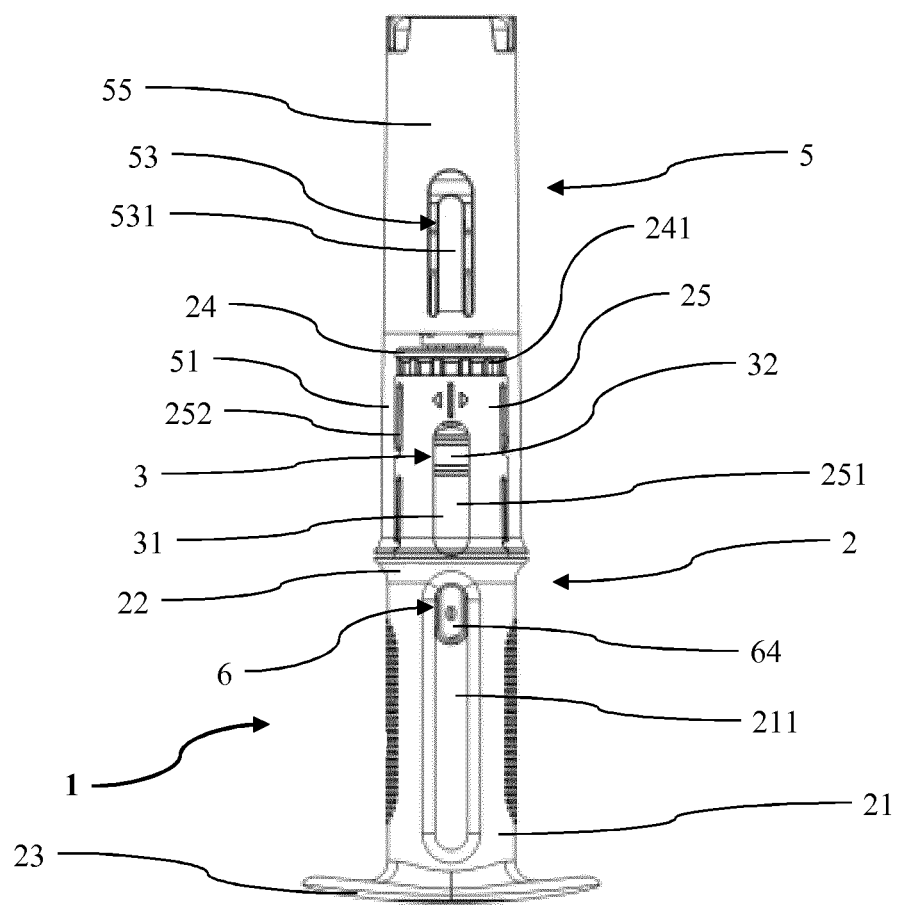
FIG. 1 shows a front view of a first embodiment of a medical delivery device according to the invention in a dosing status while being in a start position.

FIG. 1 shows a first embodiment of a medical delivery device 1 according to the invention in a dosing status. The medical delivery device 1 comprises a dosing activator 5 and an injection device. The injection device has a housing 2 with a distal body section 21 and a proximal body section 25. The housing 2 has an interior, a distal opening provided at a finger flange 23 positioned at a distal end side of the housing 2 and a proximal opening provided at a proximal end side 24 of the housing 2. Adjacent to the end side 24 the body 2 is provided with a plurality of grooves 241 at an outer circumference. The distal body section 21 is equipped with an axial indicator window 211 and the proximal body section 25 with an axial chamber window 251 vertically above the indicator window 211. The proximal body section 25 further has a pair of retaining arms 252.

In the interior of the housing 2 a rod element 3 with a vertically aligned stem 31 and a rubber stopper 32 at the lower end of the stem as well as a dosage member 6 with a highlighting element 64 are arranged. The stem 31 and the rubber stopper 32 are visible through the chamber window 251 of the proximal body section 25 of the housing 2. The highlighting element 64 of the dosage member 6 is held and guided in the indicator window 211 of the distal body section 21. The distal body section 21 and the proximal body section 25 are separated by an abutting ring 22 of the housing 2. The abutting ring 22 has a horizontal upper surface.

The upper body section 25 of the housing 2 is encased by a transparent sleeve portion 51 of the dosing activator 5. The sleeve portion 51 is formed as a vertically extending hollow cylinder which, in the start position shown in FIG. 1, surrounds the upper body section 25 of the housing 2. The dosing activator 5 further comprises a cylinder portion 55 and a vial seat 53 with a neck holder 531 having plural retaining arms. The cylinder portion 55 vertically extends from the sleeve portion 51 in an upward direction. The vial seat 53 is located inside and as part of the cylinder portion 55.

Figure 2:
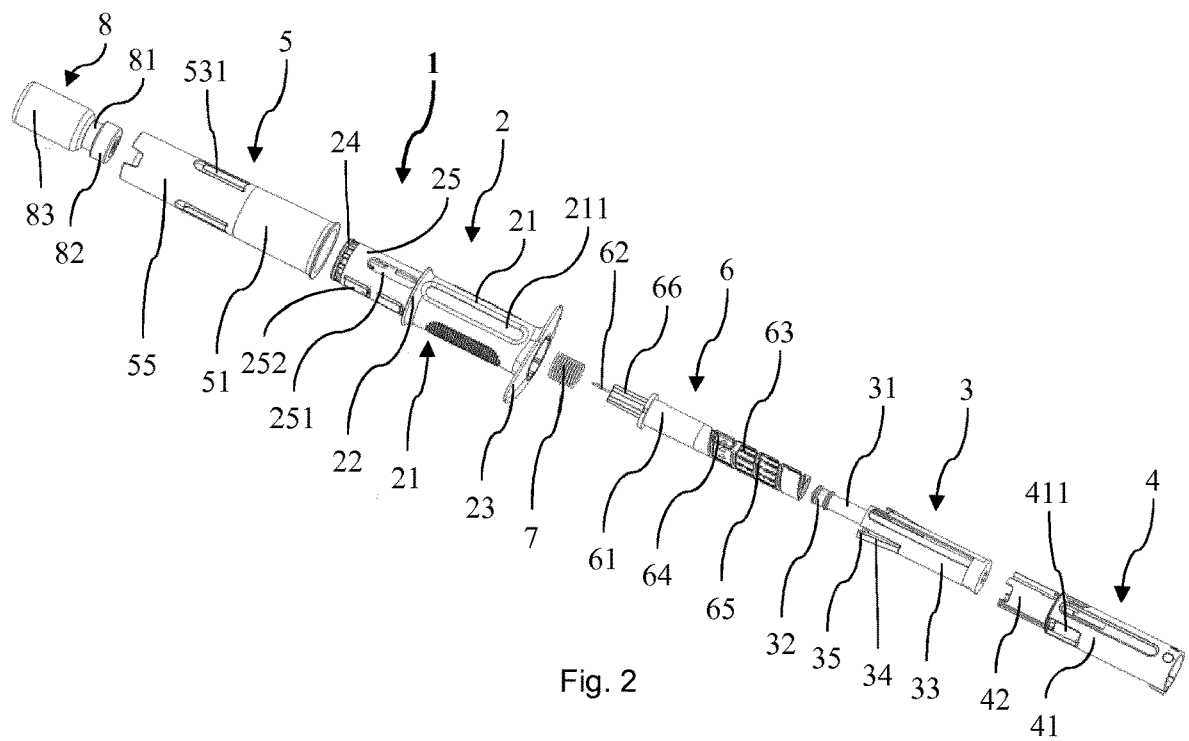
FIG. 2 shows a perspective exploded view of the medical delivery device of FIG. 1.

In FIG. 2 the medical delivery device 1 is shown in an exploded view such that single parts are visible. The medical delivery device 1 is designed to receive a vial 8 as a container. In a common manner the vial 8 has a body 83 and a neck 81 which is closed by a cap 82. In the interior of the body 83 a liquid medicament is stored which is to deliver or inject by means of the injection device.

The rod element 3 comprises a hollow body portion 33 which coaxially extends to and partially surrounds the stem 31. In a proximal direction the body portion 33 passes over into arm sections 34. Each of the arm sections 34 is at its proximal end equipped with a pin 35 projecting towards the stem 31 in an essentially radial direction. The pins 35 form male members of a first thread arrangement of the rod element 3. The pins 35 are to a certain extent flexibly mounted at the arm sections 34 in order to allow to be forced inwardly, i.e. into the direction of a longitudinal axis 38 of the rod element 3.

The dosage member 6 of the medical injection device 1 is transparent and comprises a hollow chamber cylinder 61 as chamber body with an outer surface. At the outer surface of the chamber cylinder 61 a thread 65 runs. Further, the outer surface 61 is provided with a dosage marking 63. The interior of the chamber cylinder 61 is dimensioned to receive the stem 31 and the rubber stopper 32 of the rod element 3. Thereby, the rubber stopper 32 is dimensioned to tightly fit into the interior of the chamber cylinder 61. At its proximal end the chamber cylinder 61 passes over into a male coupling structure 66 and proximally projecting therefrom a delivery needle 62. Between the dosage member 6 and the housing 2 a spring 7 is positioned.

The medical injection device further comprises a switch activator 4 having a release shell 41 and two support sections 42. The release shell 41 is equipped with two axially extending longitudinal recesses 411 of a disengaging structure. It further has a hollow interior which is dimensioned to receive the rod element 3. In particular, when the release shell 41 and its recesses 411 are arranged on the rod element 3, the arm sections 34 of the rod element 3 are pressed inwardly unless the release shell 6 is rotated around the rod element 3 such that the arm sections 34 lie in the recesses 411 as explained in more detail below.

Figure 3:
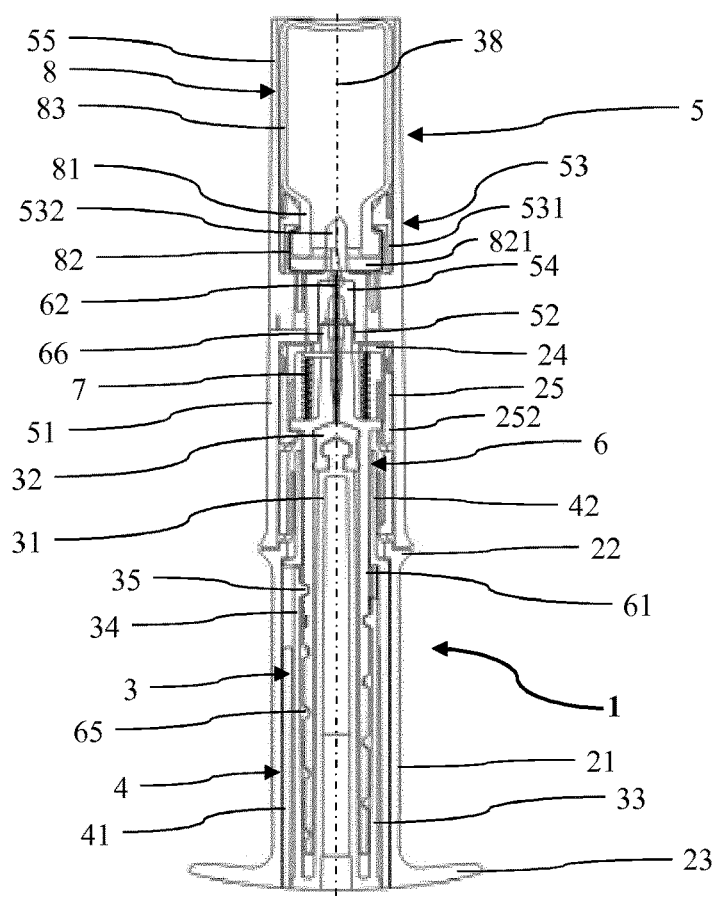
FIG. 3 shows a cross sectional view of the medical delivery of FIG. 1.

FIG. 3 shows the assembled medical delivery device 1 in the start position. The medical delivery device 1 is presented in an upright alignment such that the proximal end is at the top and the distal end at the bottom. The switch activator 4 extends inside the hollow interior of the distal body section 21 of the housing 2. The rod element 3 vertically extends through the switch activator 4. The stem 31 and the rubber stopper 32 of the rod element 3 are arranged inside the chamber cylinder 61 of the dosage member 6. More particularly, the chamber cylinder 61 is positioned between the stem 31 and the body portion 33 or arm sections 34 of the rod element 3. The arm sections 34 are pressed towards a longitudinal axis 38 of the stem 31 of the rod element 3 by the release shell 41 such that the pins 35 horizontally project towards the stem 31 and are located inside the thread 65 of the dosage member 6. Like this, the pins 35 engage the thread 411.

In FIG. 3 the longitudinal axis 38 vertically extends. It corresponds to the longitudinal axis of the housing 2, the switch activator 4, the dosing activator 5, the dosage member 6, the spring 7 and the overall device 1. The stem 31 of the rod element 3 has a head bulb at its proximal end onto which the rubber stopper 32 is put.

The sleeve portion 51 of the dosing activator 5 is arranged top down on the proximal body section 25 of the housing 2. Thereby, the distal end of the dosing activator 5 abuts the horizontal surface of the abutting ring 23 of the housing 2. In the interior of the housing 2 a barrier with an opening is arranged between the sleeve portion 51 and the cylinder portion 55. The rod element 3 abuts this barrier such that the male coupling structure 66 extends through the opening of the barrier into the cylinder portion 55 of the dosing activator 5. Adjacent to the barrier the dosing activator 5 comprises a female coupling structure 52 which fits and inter-engages with the male coupling structure 66 of the dosage member 6.

The dosage member 6 together with the rod element 3 and the switch activator 4 are arranged inside the housing 2. Thereby, the retaining arms 252 of the proximal body section 25 hold a collar of the dosage member 6 which collar is arranged between the chamber cylinder 61 and the male coupling structure 66. Like this, the housing 2 is mounted to the dosage member 6, the rod element 3 and the switch activator 4. Between the collar of the dosage member 6 and the barrier of the housing 2 the spring 7 is arranged. Thereby, the spring 7 is pre-stressed.

Inside the hollow interior of the cylinder portion 55 of dosing activator 5 the vial seat 53 is positioned. Besides the neck holder 531 with its retaining arms it comprises a vial rest and a spike 532 vertically projecting in an upward direction from the vial rest. In a step of preparing the medical delivery device 1, the vial 8 is pressed top down into the dosing activator 5 and its vial seat 53. Thereby, the retaining arms of the neck holder 531 are moved in an outward direction such that a head of the vial 8 with the cap 82 passes flange ends of the retaining arms. Once the vial 8 is sufficiently pressed down, the flange ends of the retaining arms snap behind the head and in the neck 81 of the vial 8 such that the vial 8 is safely held. In this way, the vial 8 is vertically mounted top down in the medical delivery device 1.

While the vial 8 being pressed into the vial seat 53 a tip of the spike 532 penetrates the cap 82 including a septum 821. Below the spike 532 a tip of the delivery needle 62 is arranged. The delivery needle 62 is covered by a needle seal 54. The delivery needle extends from the spike 532 through the male coupling structure 66 into the interior of the chamber cylinder 61. Like this, in the start position shown in FIG. 3, the spike 532 together with the delivery needle 62 form an open duct as transfer channel between the interior of the vial 8 and the interior of the chamber cylinder 61 of the dosage member 6. Thereby, the needle seal 54 allows for minimizing or eliminating the free space between the delivery needle 62 and the spike 532.

Figure 4:
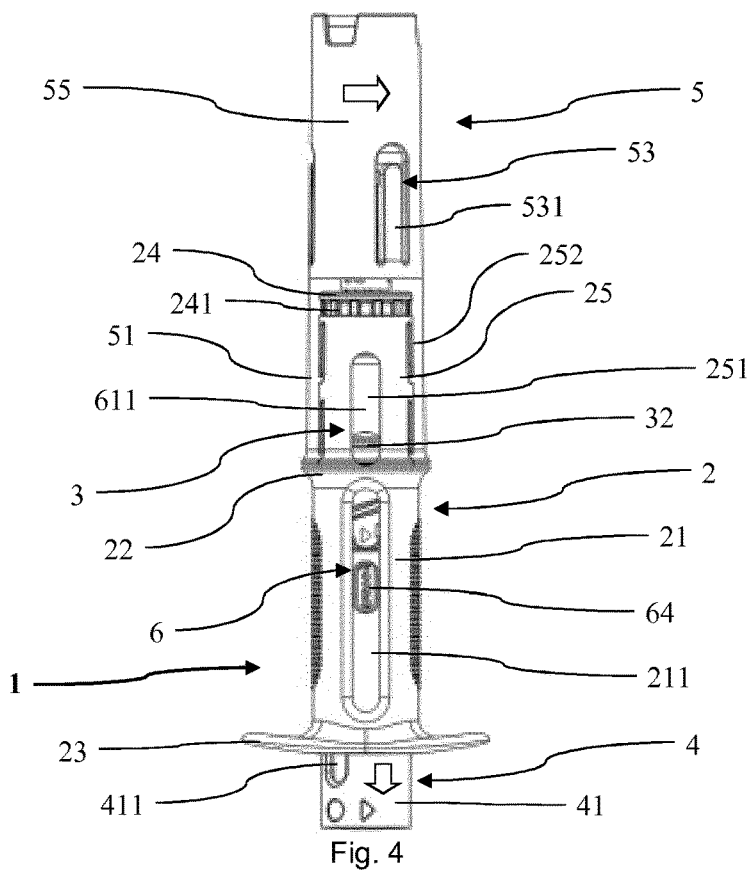
FIG. 4 shows a front view of the medical delivery device of FIG. 1 in the dosing status after dosing.
Figure 5:
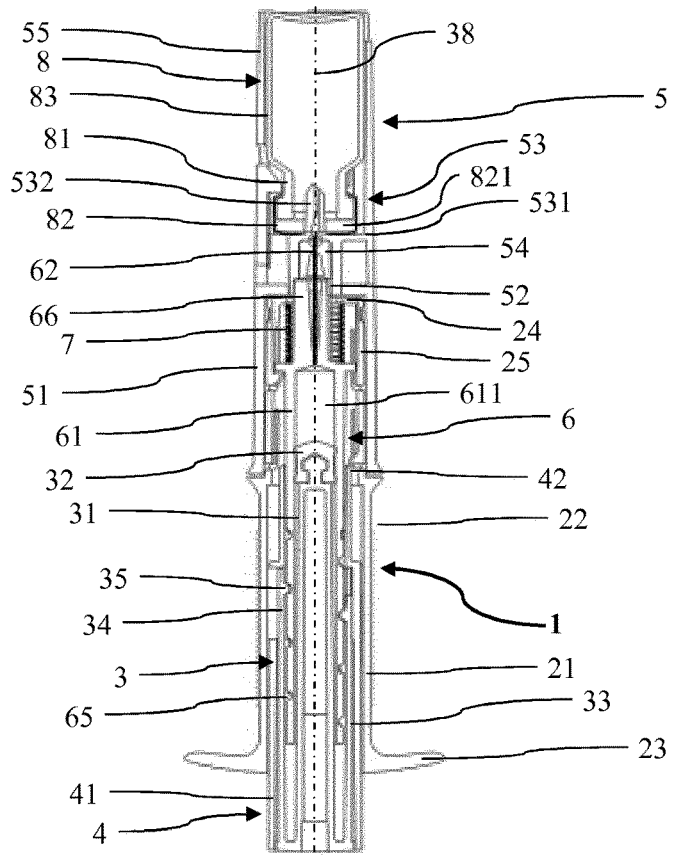
FIG. 5 shows a cross sectional view of the medical delivery device of FIG. 4.

FIG. 4 and FIG. 5 show the medical delivery device 1 after dosing, i.e. after transferring a specific amount of the medicament from the vial 8 into a dosage chamber 611 of the chamber cylinder 61 of the dosage member 6. As indicated by the upper arrow in FIG. 4, for dosing the dosing activator 5 is rotated anti-clockwise relative to the housing 2. Thereby, the housing 2 can be held at its distal body section 21 by one hand of a patient and with the other hand the patient can rotate the cylinder portion 55 of the dosing activator 5 relative to the housing 2. For matter of convenience, the outer surface of the distal body section 21 is provided with gripping ribs. Since the dosage member 6 is connected to the dosing activator 5 in a torque-resistant manner via the male coupling structure 66 and the female coupling structure 52, the dosage member 6 is rotated together with the dosing activator 5. Thus, the dosage member 6 rotates relative to the rod element 3 causing the pins 35 to travel along the thread 65. Like this, as indicated by the lower arrow, the rod element 3 is downwardly moved along the longitudinal axis 38 of the stem 31.

When axially moving the rod element 3 in a downward direction, the dosing chamber 611 between the rubber stopper 32 and the distal end of the chamber cylinder 61 of the dosage member 6 is generated and increased. In the meantime, an underpressure is created in the dosing chamber 61 such that the medicament is sucked from the vial 8 through the spike 532 and the delivery needle 62 into the dosing chamber 611. The size of the dosing chamber 611 corresponds to the amount of rotation of the dosing activator 5 which causes the rod element 3 to move downwardly or distally.

The grooves 241 at the outer circumference of the housing 2 interact with the sleeve 51 of the dosing activator 5 when being rotated. Thereby, while the sleeve 51 is rotated by a specific amount or angle a click signal is induced which can be heard and felt by the patient. Thus, when the patient rotates the dosing activator 5 and notices a click he knows that the dosed volume of medicament has changed by the predefined volume. Such predefined volume can, e.g., be 25 µl.

When the dosing activator 5 rotates relative to the housing 2 during dosing, the number visible in the highlighting element 64 of the dosage member 6 changes in correspondence with the volume of the dosing chamber 611. More particularly, the highlighting element 64 is on one hand guided in the indicator window 211 such that it is axially or vertically movable relative to the housing 2 but not tangentially. On the other hand the highlighting element 64 is connected to the thread 65 via a respective rib engaging in the thread 65. Thus, when the dosing activator 5 rotates relative to the housing 2, the highlighting element 64 is vertically moved by the rib interacting with thread 65. Compared to FIG. 1 in which the highlighting element 64 is at the top end of the indicator window 211, in FIG. 4 it is downwardly moved and lies over the numeral of the dosage marking corresponding to the volume of the dosing chamber 611.

The dosing activator 5 can be rotated in both directions. Thereby, an anti-clockwise rotation causes the dosage volume 611 to increase and, vice versa, a clockwise rotation causes the dosage volume 611 to decrease such that the medicament is transferred back to the vial 8.

Figure 6:
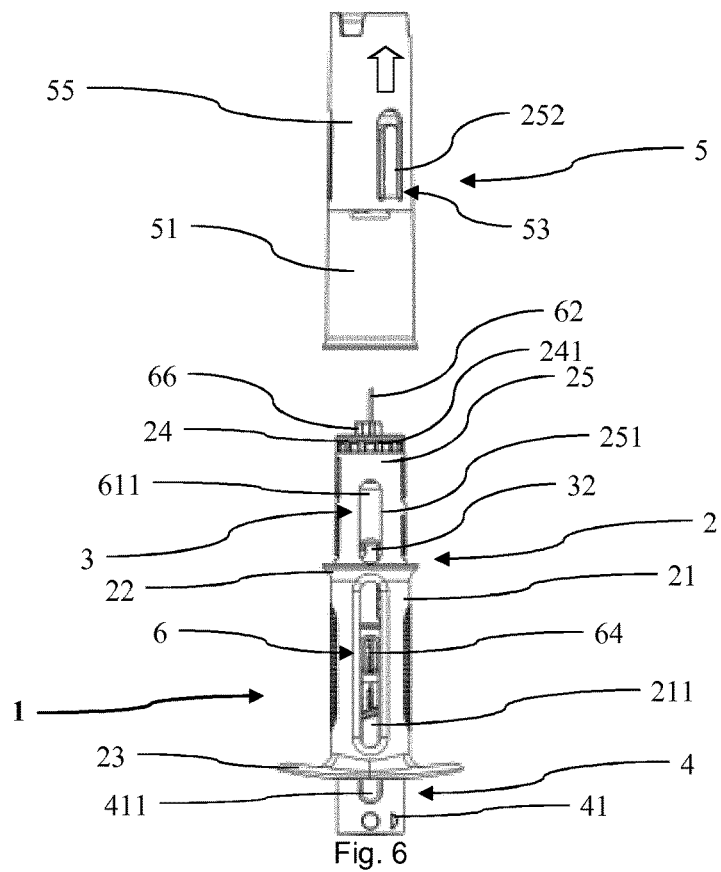
FIG. 6 shows a front view of the medical delivery device of FIG. 1 after removal of a dosing activator from an injection device.
Figure 7:
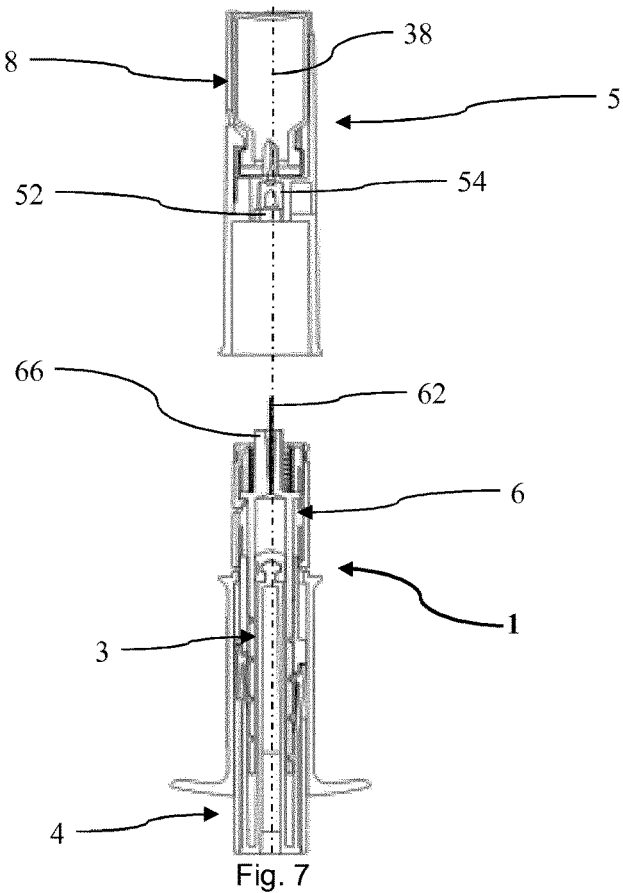
FIG. 7 shows a cross sectional view of the medical delivery device of FIG. 6.

In FIG. 6 and FIG. 7 the medical delivery device 1 is shown after dosing wherein the dosing activator 5 together with the vial 8 is removed. As indicated by the arrow in FIG.

6, once the dosage is set as described above the dosing activator 5 is upwardly or proximally pulled off the housing 2 by the patient or user. Thereby, the male coupling structure 66 of the dosage member 6 disengages the female coupling member 52 of the dosing activator 5. Also the needle seal 54 being connected to the rest of the dosing activator 5 is pulled off the needle 62 such that the needle 62 is exposed.

Figure 8:
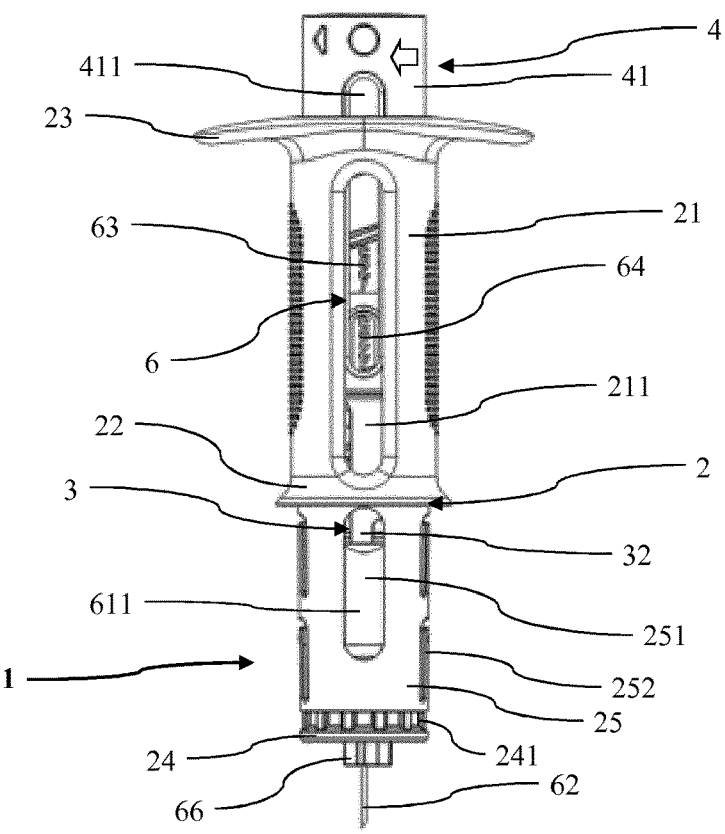
FIG. 8 shows a front view of the injection device of the medical delivery device of FIG. 1 after being switched from the dosing status to a delivery status.
Figure 9:
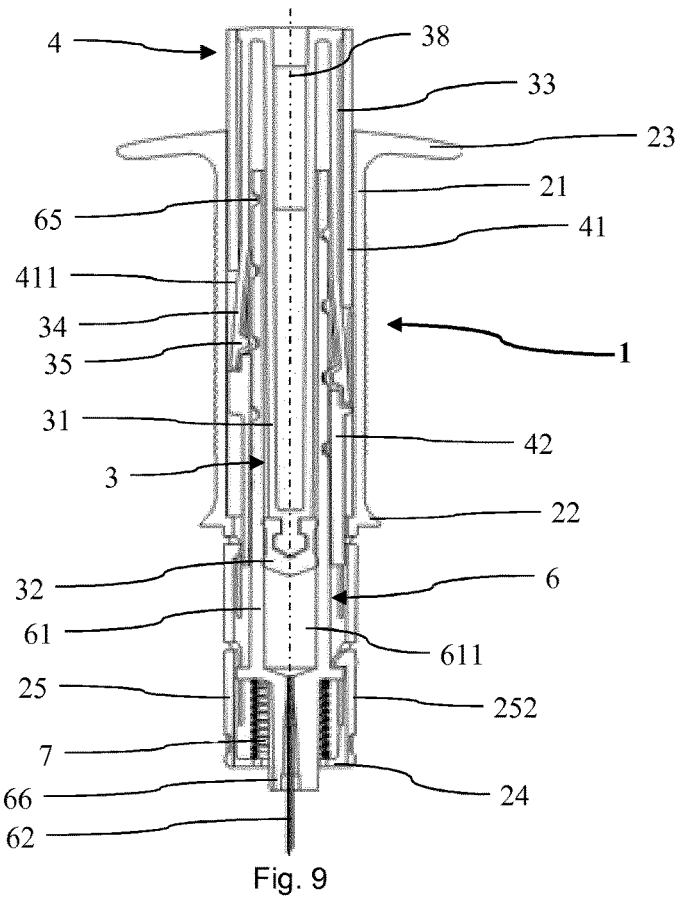
FIG. 9 shows a cross sectional view of the injection device of FIG. 8.

FIG. 8 and FIG. 9 show the injection device after being switched from the dosing status into the delivery status ready to inject the medicament. As indicated by the arrow in FIG. 8, for switching the switch activator 4 is rotated clockwise relative to the housing 2 and relative to the rod element 3. Thereby, the housing 2 can again be held at its distal body section 21 by one hand of the patient and with the other hand the patient can rotate the switch activator 4 relative to the housing 2.

The mentioned rotation of the switch activator 4 causes the recesses 411 of its release shell 41 to be aligned with the arm sections 34 of the rod element 3. Thereby, the previously radially tensioned arm sections 34 are outwardly moved away from the dosage member 6 such that the pins 35 are removed from and disengage the thread 65. In the delivery status shown in FIG. 7, the pins 35 are completely disengaged from the thread 65. Thereby, an axial movement of the rod element 3 is no longer prevented by the pins 35. Also, a further or back rotation of the switch activator 4 is blocked by the flexible ratchet arm at the distal end of the rod element 3 which rotates in a minimum dose interlock recess of the switch activator 4. Thus, once the delivery device 1 is switched into the delivery status it can not be switched back to the dosing status.

Figure 10:
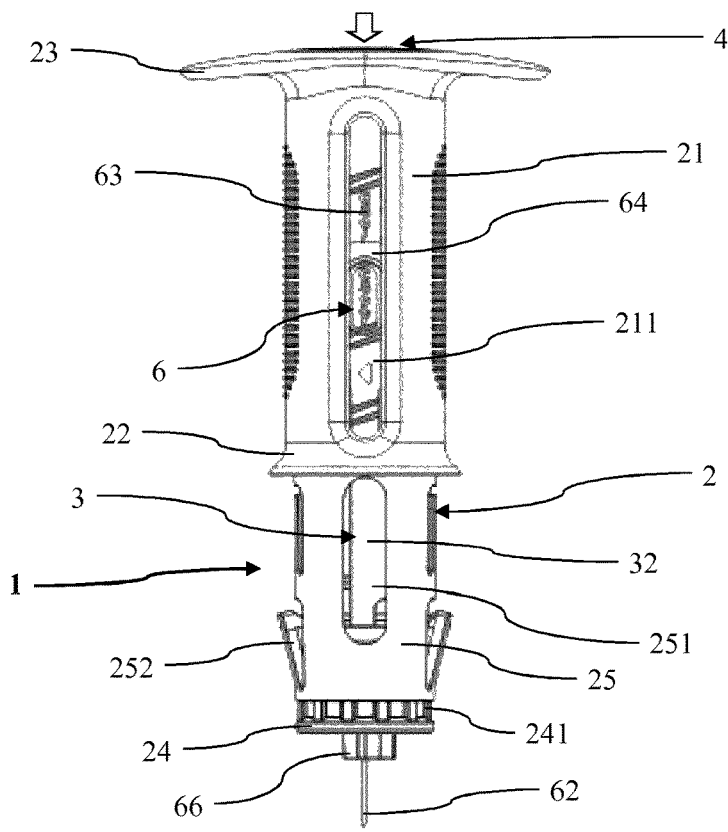
FIG. 10 shows a front view of the injection device of the medical delivery device of FIG. 1 in the delivery status after delivery.
Figure 11:
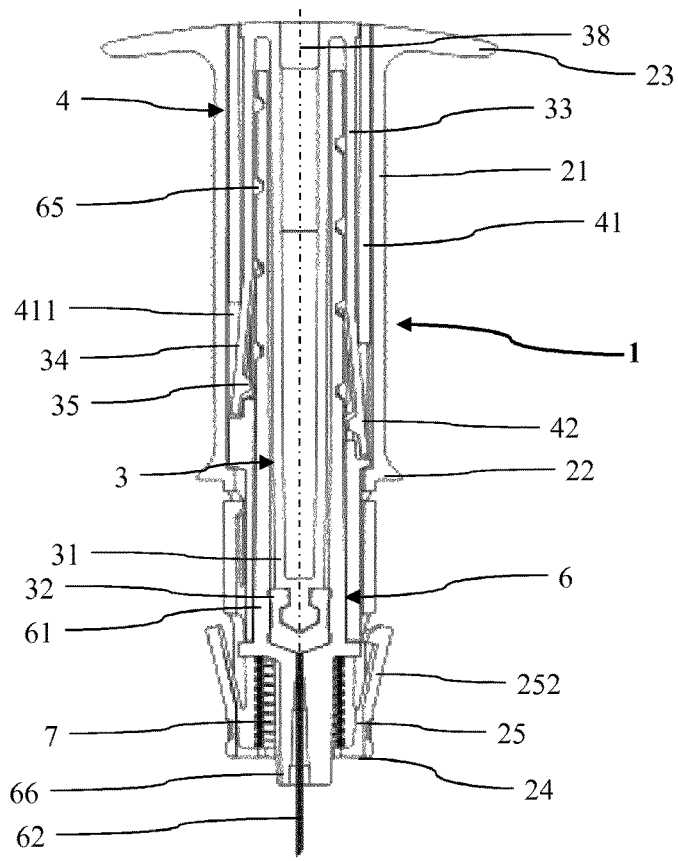
FIG. 11 shows a cross sectional view of the injection device of FIG. 10.

In FIG. 10 and FIG. 11 the injection device is shown in its delivery status after injection. Compared to the preceding Figs., in FIG. 10 and FIG. 11 the injection device is turned upside down by 180°. As indicated by the arrow in FIG. 10 the switch activator 4 is moved downwardly. More particularly, for injecting the medicament an axial force is applied on the distal end of the switch activator 4. For example, such axial force can be provided by a thumb of a hand of the patient wherein the housing 2 is held by the patient. During injection, the axial force is transmitted from the switch activator 4 to the rod element 3 such that its rubber stopper 32 is pressed into the dosage chamber 611 and the medicament is supplied out of the delivery needle 62. After injection, as shown in FIG. 11, the volume of the dosage chamber 611 is minimized such that the medicament is essentially completely delivered.

Figure 12:
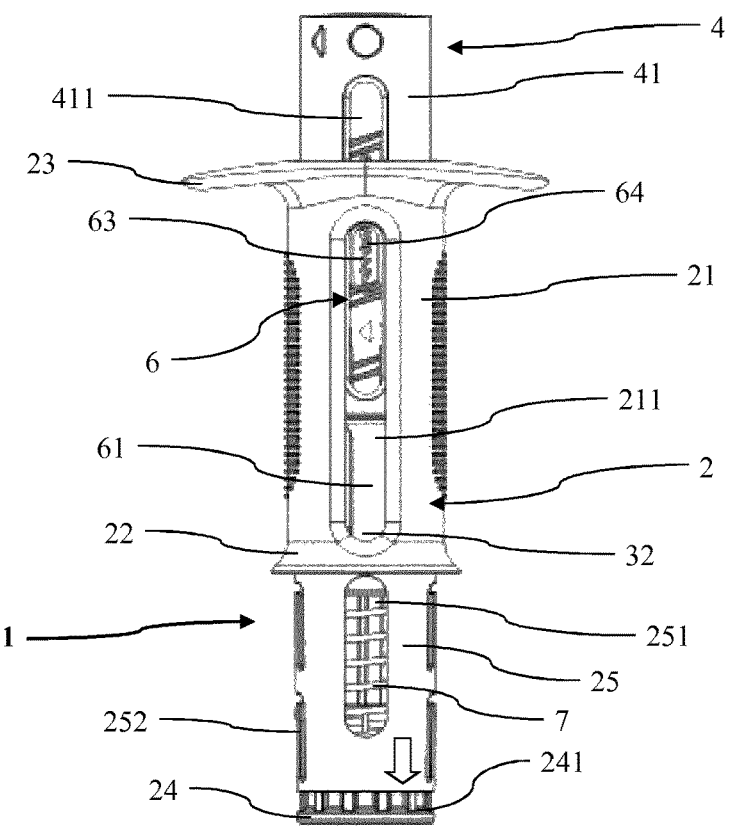
FIG. 12 shows a front view of the injection device of the medical delivery device of FIG. 1 in the delivery status after a needle being covered and protected.
Figure 13:
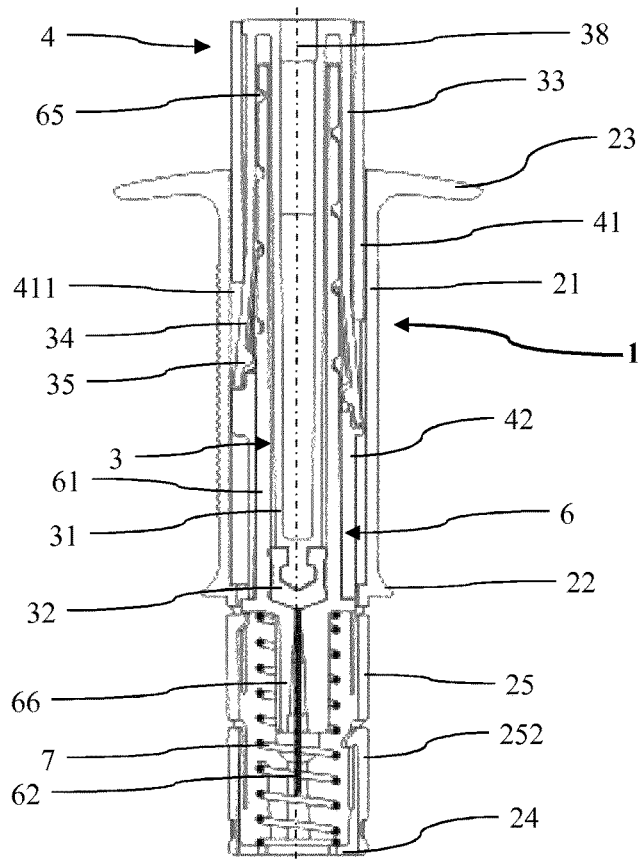
FIG. 13 shows a cross sectional view of the injection device of FIG. 12.

Additionally, while axially moving the rod element 3 in a downward direction, the retaining arms 252 of the proximal body section 52 of the housing 2 are pressed outwardly off the direction of the axis 38 by the support section 42 of the switch activator 4. After injection, the retaining arms 252 are completely disengaged from the collar of the dosage member 6 such that the housing 2 and the dosage member 6 are disconnected from each other. As shown in FIG. 12 and FIG. 13 this allows the spring force of the spring 7 initially being pre-stressed between the housing 2 and the dosage member 6 to axially move the housing 2 in relation to the other parts of the injection device and particularly also in relation to the needle 62. Like this, the needle 62 is retracted and therefore completely covered by the housing 2 which can prevent injuries by the needle 62 after injection.

Figure 14:
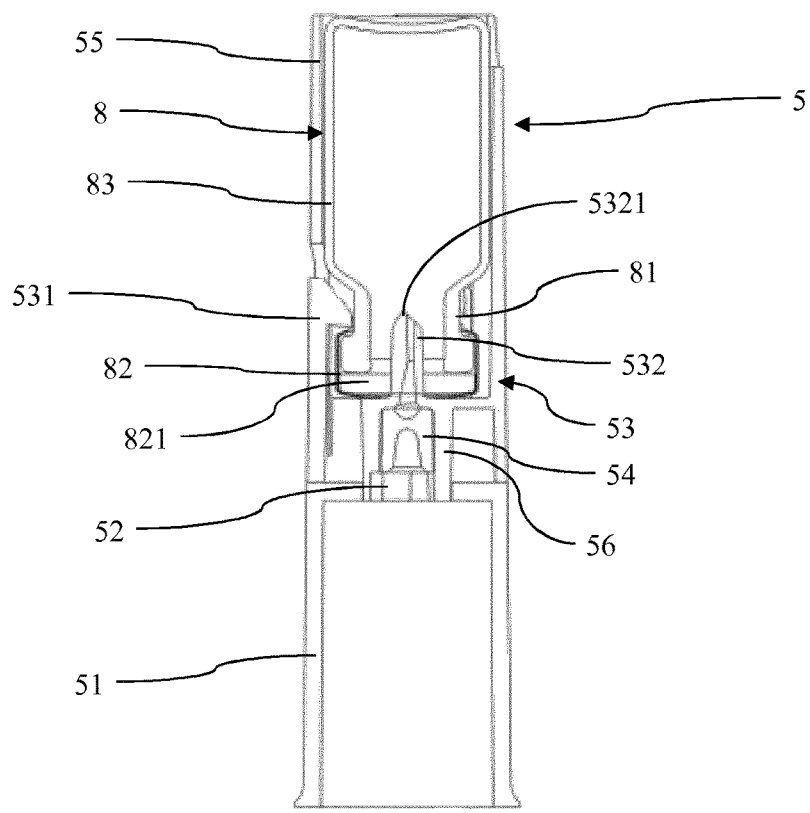
FIG. 14 shows a cross sectional view of the dosing activator of FIG. 1 removed from the injection device.

FIG. 14 shows the dosing activator 5 with the vial 8 separated from the injection device 1. As can be seen the female coupling structure 52 has an inner contour corresponding to the male coupling structure 66 of the injection device 1. Like this, the female coupling structure 52 is designed for a torque resistant form fit connection with the male coupling structure.

Between the coupling structure 52 and the vial seat 53 the dosing activator 5 has a seal holder 56. The seal holder 56 is essentially cup shaped wherein the open side extends downwardly. Inside the seal holder 56 the needle seal 54 is arranged. The needle seal 54 is made of silicone and has a plug-like form. For being mounted it is dimensioned such that it is slightly compressed when being arranged in the seal holder 56. Like this the needle seal 54 is firmly connected to the seal holder 56.

The tip 5321 of the upwardly extending spike 53 is shaped with a sharp edge. This allows for conveniently piercing the septum 821 of the cap 82 of the vial 8. Adjacent to the sharp edge the tip 5321 has an opening being the upper end of a vertical conduit 5322. The conduit 5322 extends throughout the whole spike 532 and opens into the top end of the seal holder 56.

Figure 15:
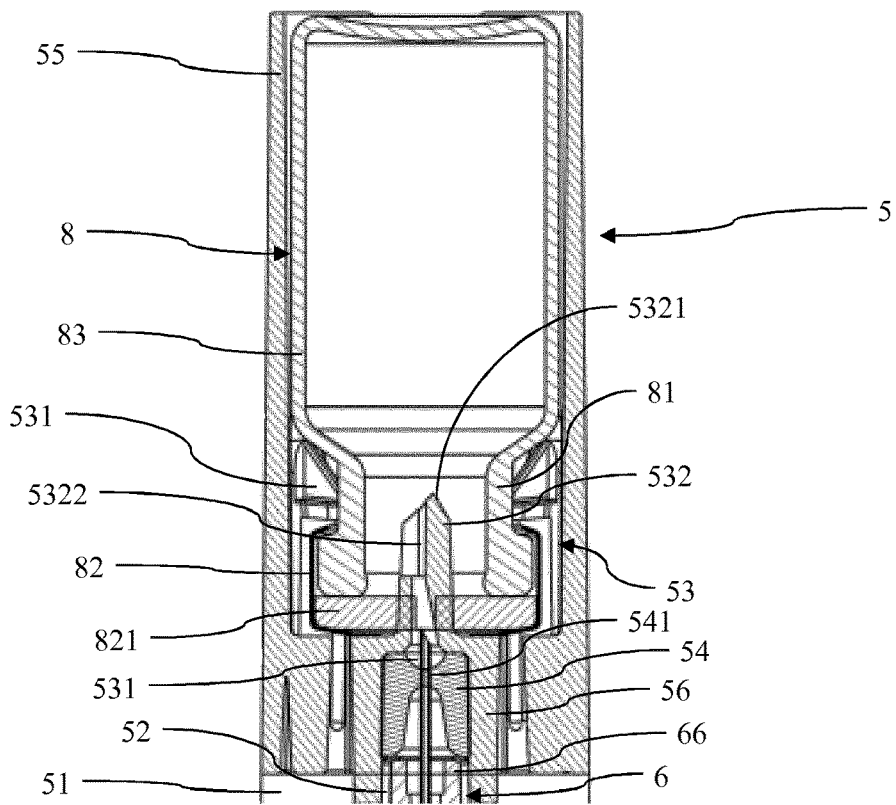
FIG. 15 shows a cross sectional view of a detail of the dosing activator of FIG. 14.

As can be seen in FIG. 15, in which the dosing adapter 5 is shown when being mounted to the injection device 1, the needle seal 54 has a vertical passage 541 through which the needle 62 of the dosing member 6 of the injection device 1 extends. The tip of the needle 62 upwardly projects slightly into a bottom section of the conduit 5322 of the spike 532. The free space around the tip of the needle 62 forms an air volume 55. The air volume 55 gives a tolerance allowing a convenient and safe mounting and demounting of the dosing activator 5 to and from the injection device 1. Nevertheless, the air volume 55 is minimized such that a minimal volume of air is involved when withdrawing the liquid from the vial 8.

Figure 16:
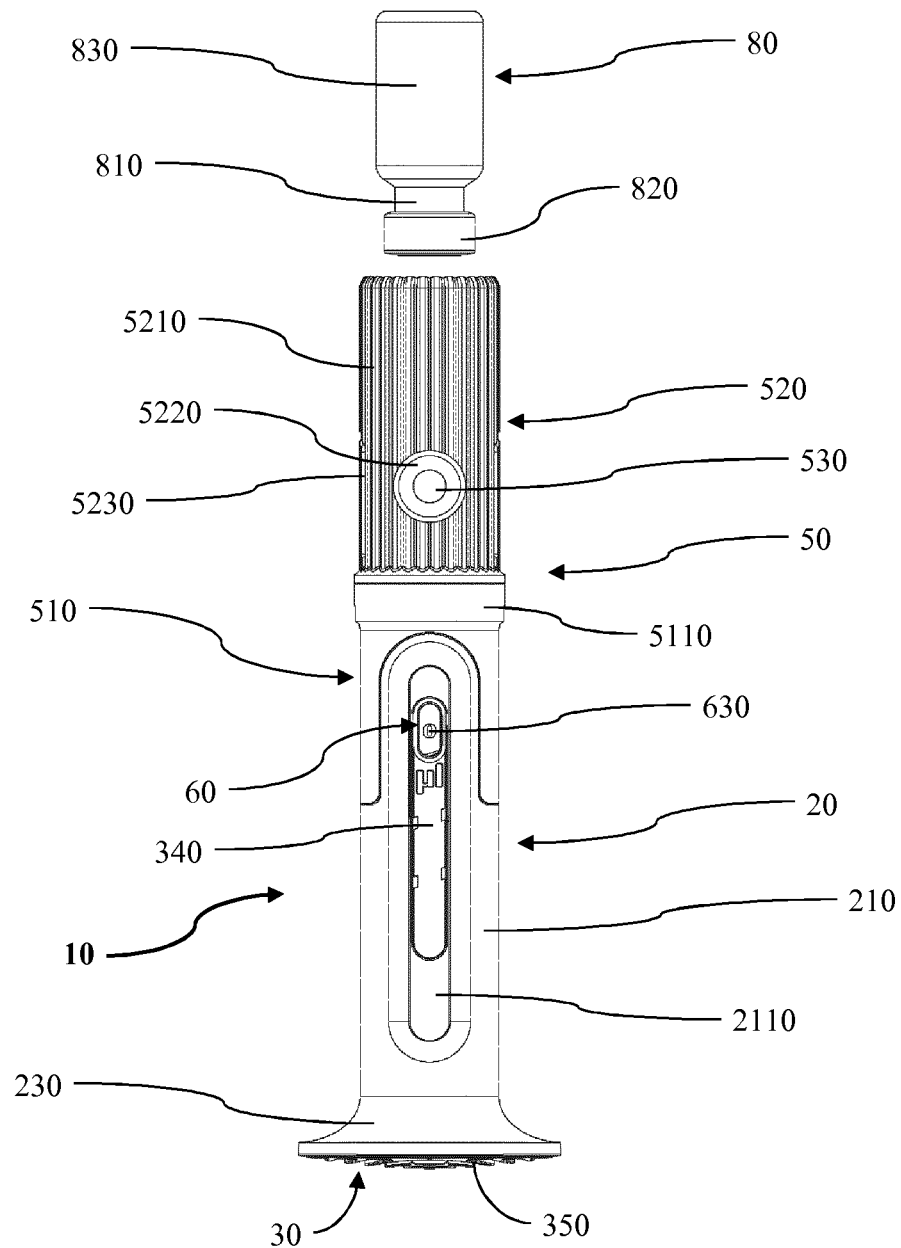
FIG. 16 shows a front view of a second embodiment of a medical delivery device according to the invention in a lock status while being in a start position.

FIG. 16 shows a second embodiment of a medical delivery device 10 according to the invention in a lock status. The medical delivery device comprises a dosing activator 50 and an injection device. The injection device has a housing 20 with a distal body section 210 passing over into a finger flange 230 at its lower or bottom end. The housing 20 has a hollow interior, a distal opening provided at the finger flange 230 and a proximal opening provided at a proximal end side 240 (not visible in FIG. 16) of the housing 20. The body section 210 is equipped with an axial indicator window 2110.

In the interior of the housing 20 a rod element 30 with a push cone 350 and a highlighting element 340 are arranged. The highlighting element 340 is held and guided in the indicator window 2110 of the body section 210. Through the highlighting element 340 a dosage marking 630 of a dosage member 60 is visible which in FIG. 16 shows zero. On the upper portion of the housing 20 a sleeve unit 510 of the dosing activator 50 is arranged. The sleeve unit 510 is formed as a vertically extending hollow cylinder with an incision which, in the start position shown in FIG. 16, surrounds the upper portion of the body section 210 of the housing 20.

The sleeve unit 510 is equipped with a dial mount ring 5110 at its top end by which it is rotatably connected to a dial unit 520 of the dosing activator 50. The dial unit 520 is essentially cylindrically shaped and vertically extends from the sleeve unit 510 in an upward direction. An outer surface of the dial unit 520 is equipped with gripping ribs 5210 for allowing a convenient manual operation. It further has a window opening 5220 through which a release member 530 of the dosing activator 50 is visible. Furthermore, the dial unit 520 is equipped with a neck holder 5230 having two snap-in arms.

The medical delivery device 10 is embodied to receive a vial 80 as a container. In a common manner the vial 80 has a body 830 and a neck 810 which is closed by a cap 820. In the interior of the body 830 a liquid medicament is stored which is to deliver or inject by means of the injection device.

Figure 17:
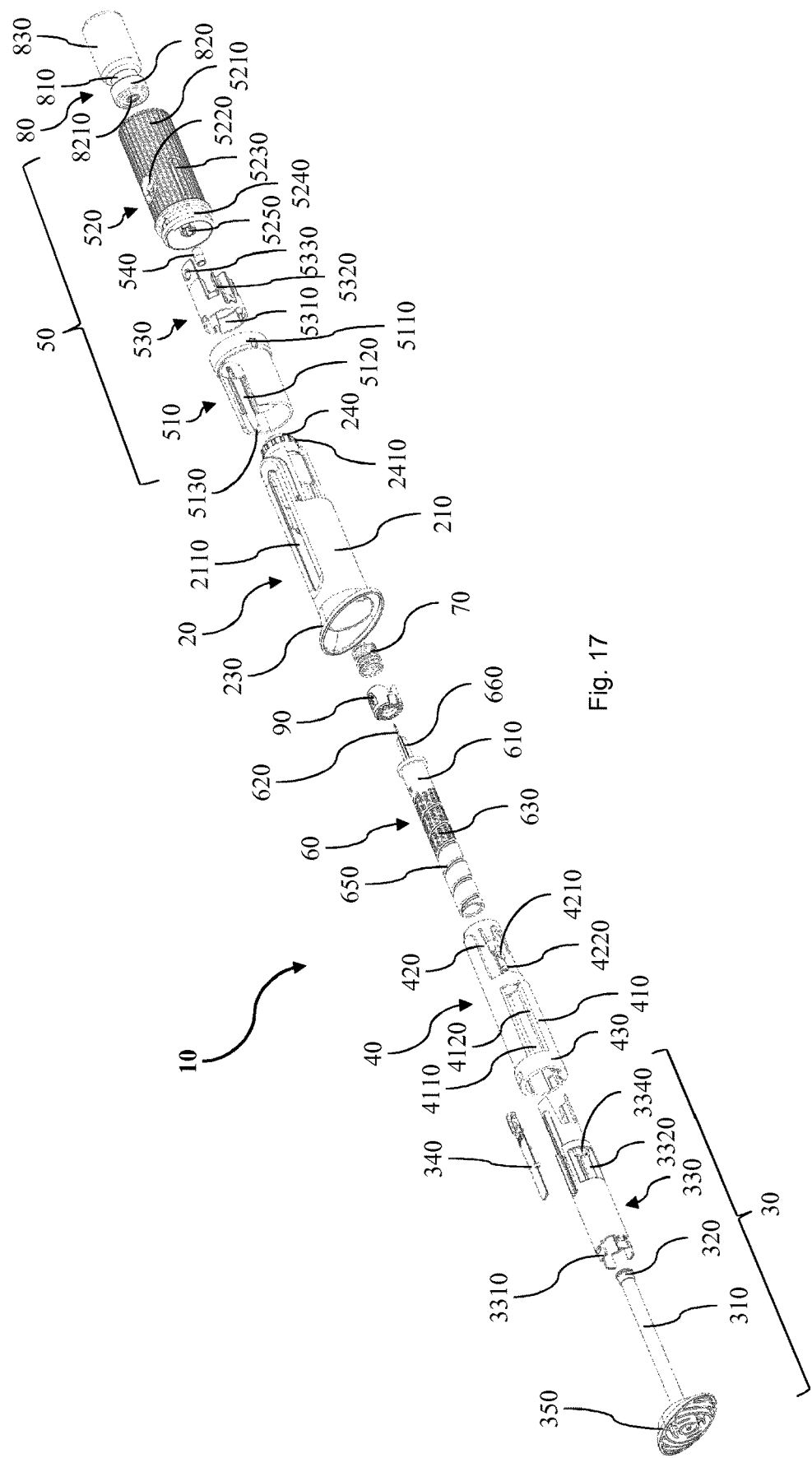
FIG. 17 shows a perspective exploded view of the medical delivery device of FIG. 16.

In FIG. 17 the medical delivery device 10 is shown in an exploded view such that single parts are visible separately. The rod element 30 comprises a hollow body portion 330 which coaxially extends to and, when mounted, surrounds a stem 310. The body portion 330 has arm sections 3320 each of which at one end is fixed to the rest of the body portion 330 and at the other end has an outwardly extending release hump 3340. Furthermore, each of the arm sections 340 is equipped with a pin 3330 (not visible in FIG. 17) projecting towards the stem 310 in an essentially radial direction. At a distal end, the body portion 330 of the rod element 30 comprises four clip latches 3310. To a proximal axial end of the stem 310 a rubber stopper 320 is mounted as shown in more detail below.

The dosage member 60 of the injection device comprises a hollow chamber cylinder 610 as chamber body. At an outer surface of the chamber cylinder 610 a thread 650 runs. Further, the outer surface 610 is provided with the dosage marking 630. The interior of the chamber cylinder 610 is dimensioned to receive the stem 310 and the rubber stopper 320 of the rod element 30. Thereby, the rubber stopper 320 is dimensioned to tightly fit into the interior of the chamber cylinder 610. At its proximal end the chamber cylinder 610 passes over into a male coupling structure 660 and, proximally projecting therefrom, a delivery needle 620. Between the dosage member 60 and the housing 20 a lockout member 90 of a release mechanism and a spring 70 are positioned.

The medical delivery device 10 further comprises a switch activator 40 having a release shell 410 radially extending from a distal base ring 430 and a sleeve recess portion 420. The release shell 410 is equipped with two axially extending longitudinal recesses 4110 limited by two axial slanting surfaces 4120 of a disengaging structure. It further has a hollow interior which is dimensioned to receive the rod element 30. In particular, when the release shell 410 and its recesses 4110 are arranged on the rod element 30, the arm sections 3320 of the rod element 30 are positioned at the recesses 4110 such that the release humps 3340 extend into the recesses 4110. As described in more detail below a rotation of the release shell 410 causes one of the slanting surfaces 4120 to act on the respective release humps 3340 such that the arm sections 3320 are lifted or radially bent. At the sleeve recess portion 420 the switch activator is further equipped with second ramps 4210 and backup members 4220.

As can be further seen in FIG. 17 the body 20 is provided with a plurality of grooves 2410 at an outer circumference adjacent to its end side 240. At a distal end the sleeve unit 510 of the dosing activator 50 comprises first ramps 5130 from which guidance tracks 5120 axially extend.

The release member 530 of the dosing activator 50 has an axial tongue section axially extending from a ring portion 5310 in a proximal direction. The axial tongue section is provided with an indicator 5330 having the shape of an arrow near its axial end. Also from the ring portion 5310 of the release member 530 two stems 5320 axially extend into the proximal direction and blocking surfaces are formed at the inside of the ring portion 5310.

In the inside of the dial unit 520 of the dosing activator 50 a female coupling structure 5250 extends into a distal direction. As can be seen more detail in the following Figs., the female coupling structure 5250 is formed to fit the male coupling structure 660 of the dosage member 60. At its distal end, the dial unit 520 further has a sleeve mount structure 5240 onto which the dial mount ring 5110 of the sleeve unit 510 can be snapped. When being connected by means of the sleeve mount structure 5240 and the dial mount ring 5110 the dial unit 520 and the sleeve unit can rotate but not axially move relative to each other.

As can also be seen in FIG. 17, the cap 820 is provided with a septum 8210. The dosing activator 50 further comprises a needle seal 540 which, as can be seen in the following Figs. in more detail, is placed inside the female coupling structure 5250 and around a tip of the needle 620 of the dosage member 60.

Figure 18:
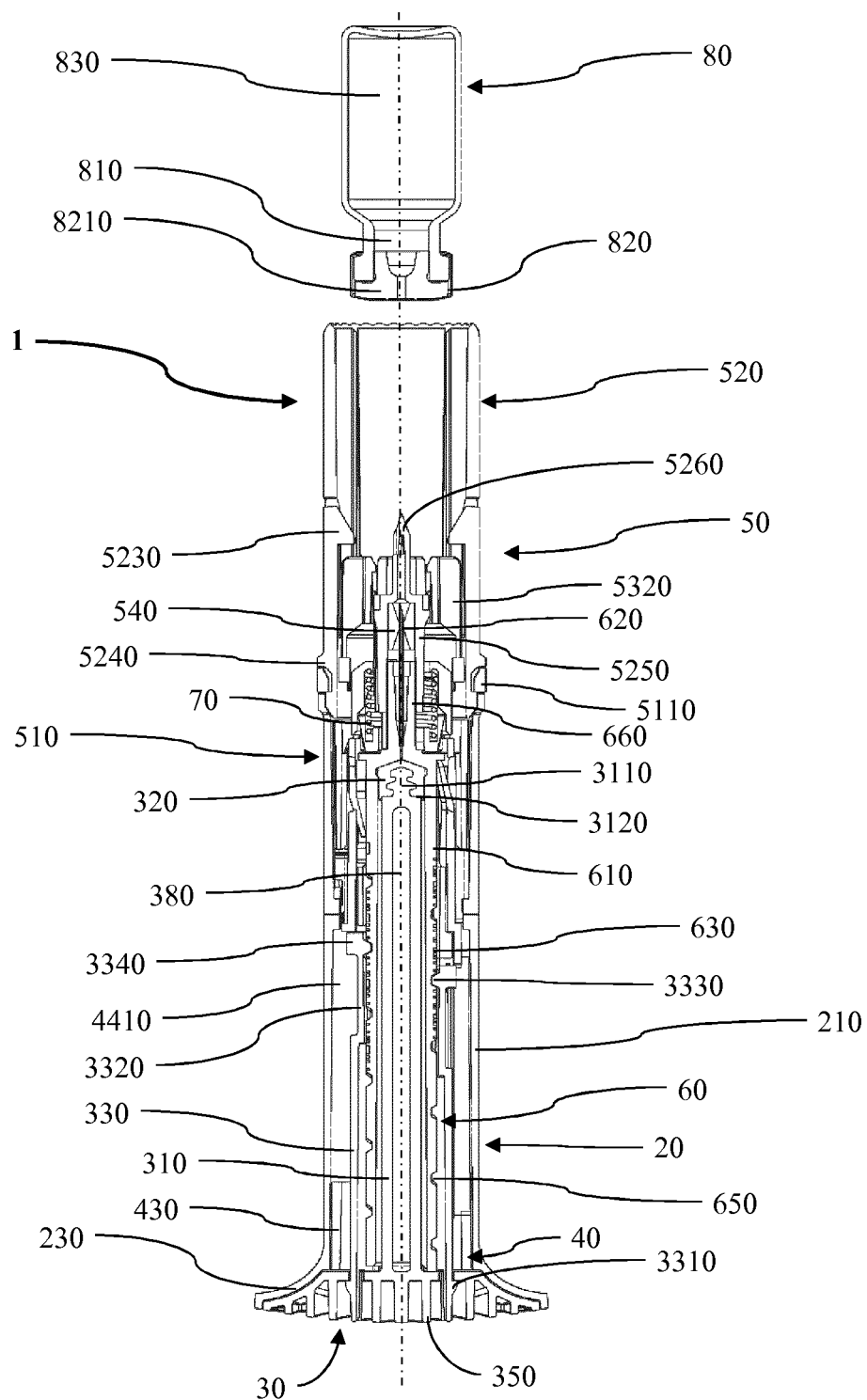
FIG. 18 shows a cross sectional view of the medical delivery of FIG. 16 in the lock status.

FIG. 18 shows the assembled medical delivery device 10 in the start position in a lock status. Thereby it is presented in an upright alignment such that the proximal end is at the top and the distal end at the bottom. The switch activator 40 extends inside the hollow interior of the distal body section 210 of the housing 20. The rod element 30 vertically extends through the switch activator 40. The clip latches 3310 of the body portion 330 of the rod element 30 are snapped in respective slits in the push cone 350 such that the stem 310, the push cone 350 and the body portion 330 are fixedly connected.

The stem 310 of the rod element 30 has a head portion 3110 which comprises two convex bulges separated by a concave intermediate section. The head portion 3110 is axially limited by an abutting face 3120 into a distal direction. The stopper 320 has an interior corresponding to the head portion 3110 of the stem 310, wherein the complete head portion 3110 is fitted into the interior of the stopper 320 such that the stopper contacts the abutting face 3120. The stem 310 and the stopper 320 of the rod element 30 are arranged inside the chamber cylinder 610 of the dosage member 60.

More particularly, the chamber cylinder 610 is positioned between the stem 310 and the body portion 330 and arm sections 3320 of the rod element 30. The pins 3330 forming male members of a first thread arrangement of the rod element 30 engage into the thread 650 as a female member of a second thread arrangement of the dosage member 60. The pins 3330 are to a certain extent flexible due to the arm sections 3320 in order to allow to be outwardly moved, i.e. away from a longitudinal axis 380 of the rod element 30. The release humps 3340 project from the arm sections 3320 in a direction opposite to the pins 3330. In the lock status, they extend into the recesses 4110 of the switch activator 40. The arms sections 3320 together with the pins 3330 and the release humps 3340 have a shape similar to a hammer.

In FIG. 18 the longitudinal axis 380 vertically extends. It corresponds to the longitudinal axis of the housing 20, the switch activator 40, the dosing activator 50, the dosage member 60, the spring 70 and the overall medical delivery device 10. The sleeve unit 510 of the dosing activator 50 is arranged top down on the body section 210 of the housing 20 wherein the housing 20 is shaped to receive the sleeve unit 510 in one single rotational alignment. In the interior of the housing 20 a barrier with an opening is arranged between the sleeve unit 510 and the dial unit 520. The rod element 30 abuts this barrier such that the male coupling structure 660 extends through the opening of the barrier into the dial unit 520 of the dosing activator 50. Adjacent to the barrier the dosing activator 50 comprises the female coupling structure 5250 which fits and inter-engages with the male coupling structure 660 of the dosage member 60. Thereby, the dial unit 520 and the dosage member 60 are torque resistantly connected.

The dosage member 60 together with the rod element 30 and the switch activator 40 are arranged and held inside the housing 20. Between a collar of the dosage member 60 and the barrier of the housing 20 the spring 70 is arranged. Thereby, the spring 70 is pre-stressed.

Inside the hollow interior of the dial unit 520 of the dosing activator 50 a vial seat is formed which comprises the neck holder 5230, a rest surface of the release member 530, a top end of the female coupling structure 5250 and a spike vertically extending from the top end of the female coupling structure 5250. The blocking surfaces of the ring portion 5310 engage the grooves 2410 as corresponding surfaces at the proximal end side 240 of the housing 20. Thereby, a rotational movement of dial unit 520 is prevented and the medical delivery device 10 is in the lock status.

Figure 19:
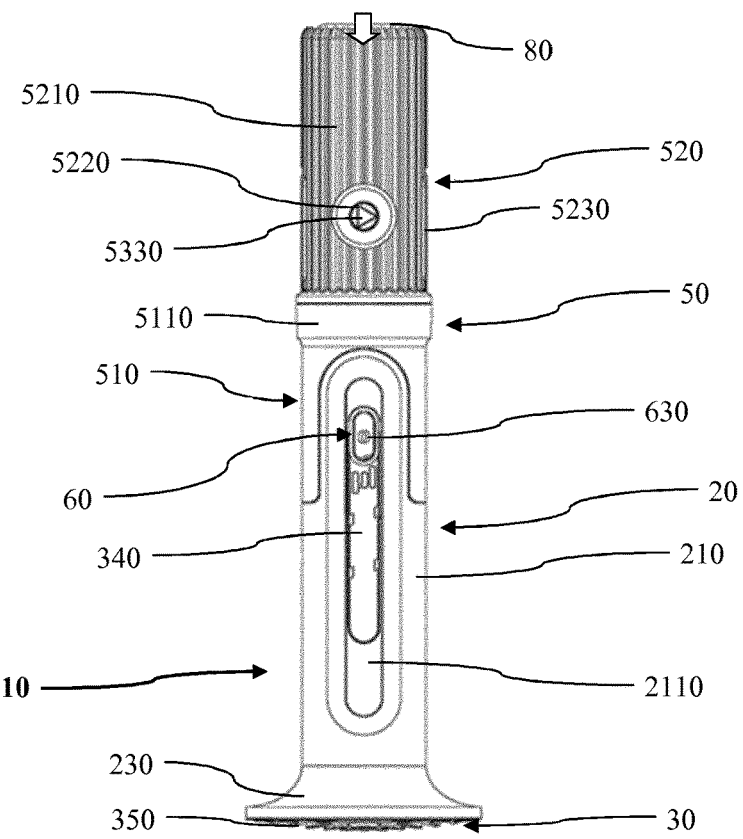
FIG. 19 shows a front view of the medical delivery device of FIG. 16 switched from the lock status to a dosing status before dosing.
Figure 20:
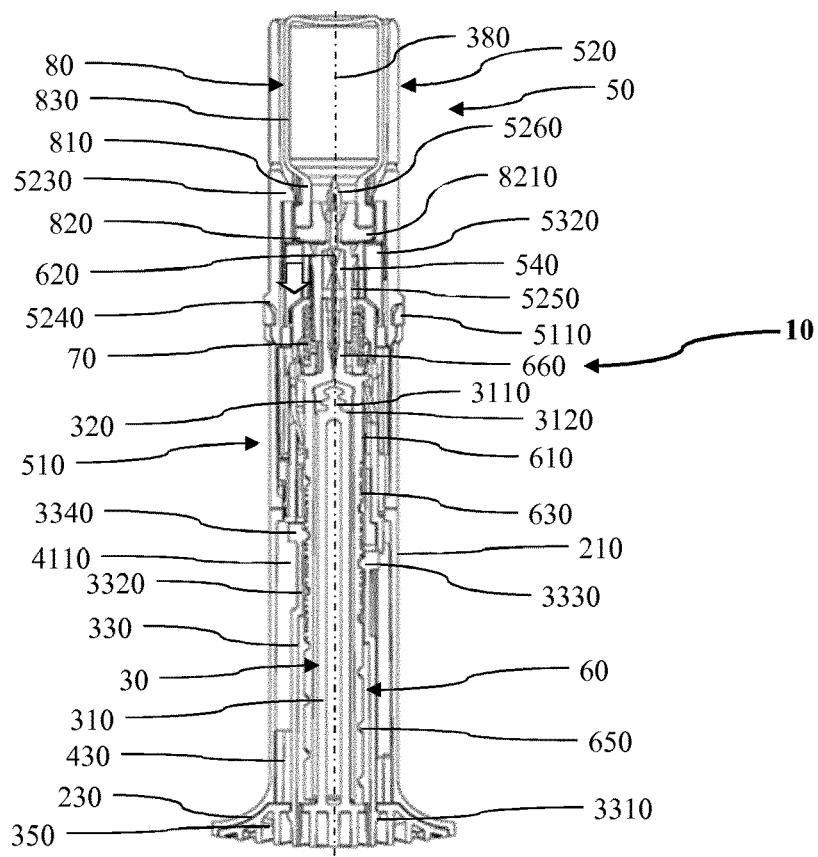
FIG. 20 shows a cross sectional view of the medical delivery device of FIG. 19.

In FIG. 19 and FIG. 20, the medical delivery device 10 is shown after being changed from the lock status to a dosing status. In a step of preparing the medical delivery device 10, the vial 80 is pressed top down into the dosing activator 50 and its vial seat. Thereby, vial 80 abuts the rest surface of the release member 530 and downwardly moves it until the blocking surfaces of the ring portion 5310 disengage the grooves 2410 of the housing 20. Like this, the dial unit 520 is made rotatable in relation to the sleeve unit 510 and the housing 20 and the medical delivery device is unlocked, i.e. in the dosing status. When the release member 530 being downwardly moved by the vial 80 the axial tongue section travels along the window opening 5220 of the dial unit 520 until the indicator 5330 is visible through the window opening 5220. Like this, a user or patient of the medical delivery device 10 is informed that the vial 80 is properly set and that the medical delivery device 10 is no longer in the lock status but in the dosing status. Also the indicator 5330 shows a direction into which the dial unit 520 is to be rotated for starting dosing.

When the vial 80 is downwardly pushed in the container seat, the retaining arms of the neck holder 5230 are moved in an outward direction such that a head of the vial 80 with the cap 820 passes flange ends of the retaining arms. Once the vial 80 is sufficiently pressed down, the flange ends of the retaining arms snap behind the head in the neck 810 of the vial 80 such that the vial 80 is safely held. In this way, the vial 80 is vertically mounted top down in the medical delivery device 10.

Furthermore, while the vial 80 being pressed into the vial seat a tip of the spike 5260 penetrates the cap 820 including the septum 8210. Below the spike 5260 a tip of the delivery needle 620 is arranged. The delivery needle 620 is partially covered by the needle seal 540. The delivery needle 620 extends from the spike 5260 through the male coupling structure 660 of the chamber cylinder 610. Like this, in the dosing status shown in FIG. 20, the spike 5260 together with the delivery needle 620 form an open duct as transfer channel between the interior of the vial 80 and the interior of the chamber cylinder 610 of the dosage member 60. Thereby, the needle seal 540 allows for eliminating leakage and minimizing the free space between the delivery needle 620 and the spike 5260. In the dosing status, the release humps 3340 of the arm sections 3320 of the rod element 30 still are positioned in the recesses 4110 of the switch activator 40. And the pins 3330 of the arm sections 3320 of the rod element 30 engage the thread 650 of the dosage member 60.

Figure 21:
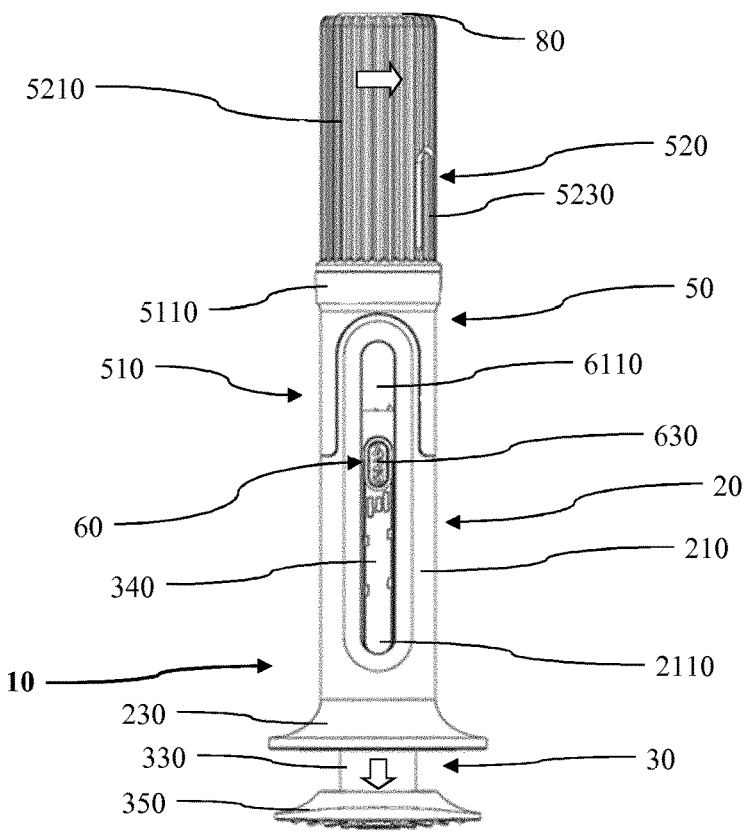
FIG. 21 shows a front view of the medical delivery device of FIG. 16 in the dosing status after dosing.
Figure 22:
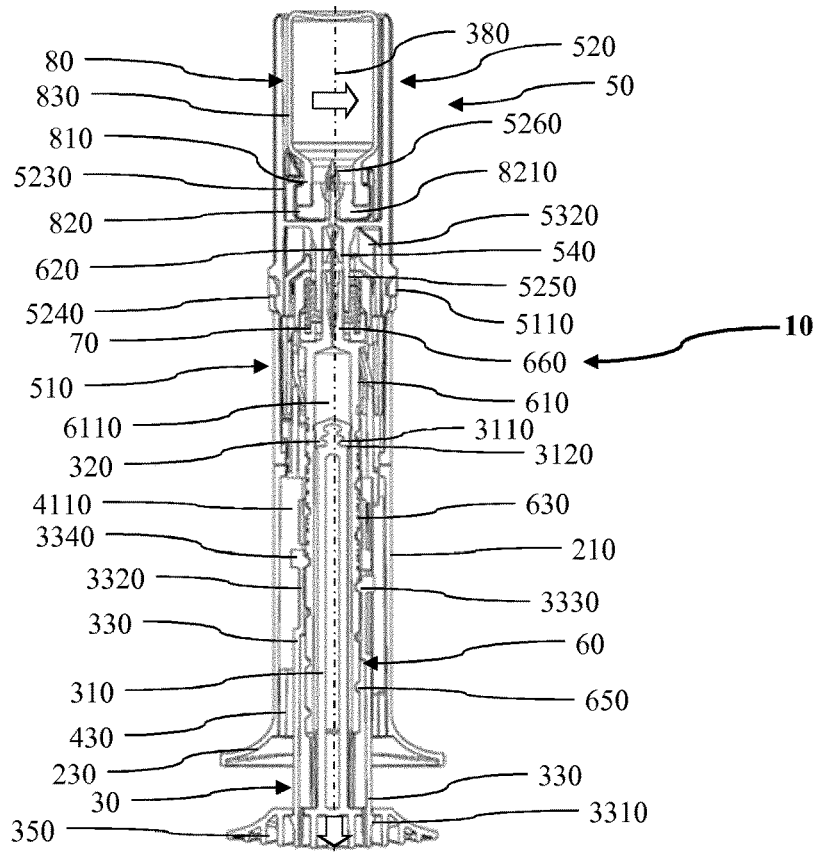
FIG. 22 shows a cross sectional view of the medical delivery device of FIG. 21.

FIG. 21 and FIG. 22 show the medical delivery device 10 after dosing, i.e. after transferring a specific amount of the medicament from the vial 80 into a dosage chamber 6110 of the chamber cylinder 610 of the dosage member 60. As indicated by the upper arrows, for dosing, the dial unit 520 of the dosing activator 50 is rotated anti-clockwise relative to the sleeve unit 510 and the housing 20. Thereby, the housing 20 can be held at its body section 210 by one hand of the user and with the other hand the user can rotate the dial unit 520 of the dosing activator 50 relative to the housing 20 and the sleeve unit 510. Since the dosage member 60 is connected to the dial unit 520 in a torque-resistant manner by the male coupling structure 660 and the female coupling structure 5250, the dosage member 60 is rotated together with the dosing activator 50. Thus, the dosage member 60 rotates relative to the rod element 30 causing the pins 3330 to travel along the thread 650. Like this, as indicated by the lower arrows, the rod element 30 is downwardly moved along the longitudinal axis 380.

When axially moving the rod element 30 in a downward direction, the dosing chamber 6110 between the rubber stopper 320 and the distal end of the chamber cylinder 610 of the dosage member 60 is generated and increased. In the meantime, an underpressure is created in the dosing chamber 610 such that the liquid or medicament is sucked from the vial 80 through the spike 5260 and the delivery needle 620 into the dosing chamber 6110. Since the head 3110 of the stem 310 of the rod element 30 is provided with the bulges 3110 the stopper 320 is firmly held and deformations caused by the underpressure are minimized or eliminated. The size of the dosing chamber 6110 corresponds to the amount of rotations of the dial shell 520 which causes the rod element 30 to move downwardly or distally.

The grooves 2410 at the outer circumference at the proximal end side 240 of the housing 20 interact with the dial unit 520 of the dosing activator 50 when being rotated. Thus, when the user rotates the dial unit 520 of the dosing activator 50 and notices a click he knows that the dosed volume of medicament has changed by the predefined volume. Such predefined volume can, e.g., be 25 µl.

When the dosing activator 50 rotates relative to the housing 20 during dosing, the number visible in the highlighting element 340 of the rod element 30 changes in correspondence with the volume of the dosing chamber 6110. More particularly, the highlighting element 340 is on one hand guided in the indicator window 2110 of the housing 20 such that it is axially or vertically movable relative to the housing 20 but not tangentially. On the other hand the highlighting element 340 is connected to the thread 650 via a respective rib engaging in the thread 650. Thus, when the dial unit 520 rotates relative to the housing 20, the highlighting element 340 is vertically moved by the rib interacting with thread 650. Compared to FIG. 19 in which the highlighting element 340 is at an upper section of the indicator window 2110, in FIG. 21 it is downwardly moved and lies over the numeral of the dosage marking corresponding to the volume of the dosing chamber 6110.

The dial shell 520 of the dosing activator 50 can be rotated in both directions. Thereby, an anti-clockwise rotation causes the dosage volume 6110 to increase and, vice versa, a clockwise rotation causes the dosage volume 6110 to decrease such that the liquid or medicament is transferred back to the vial 80.

Figure 23:
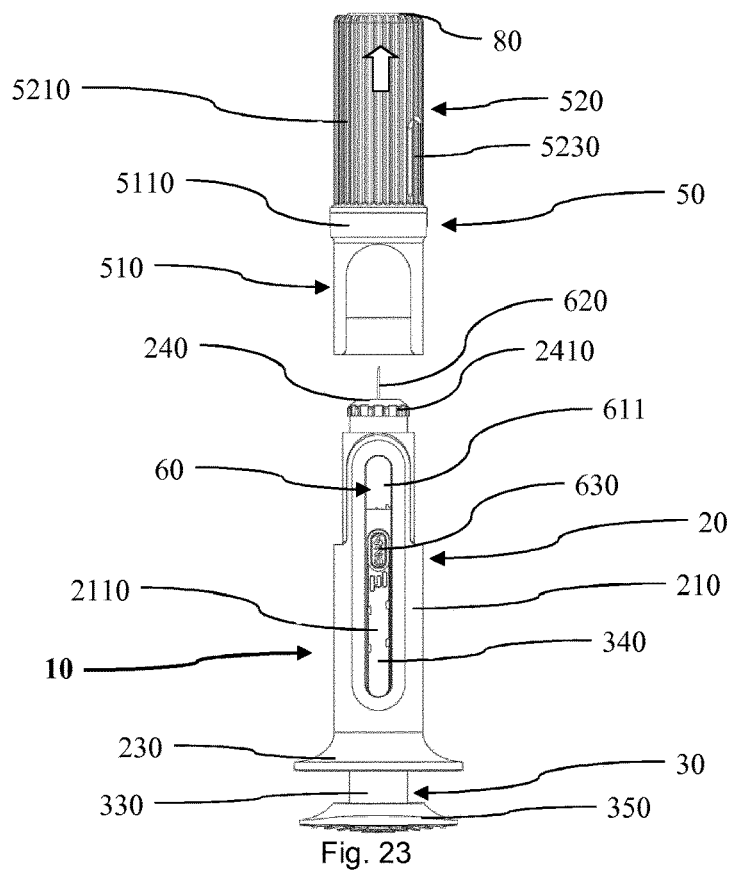
FIG. 23 shows a front view of the medical delivery device of FIG. 16 in a delivery status after removal of a dosing activator.
Figure 24:
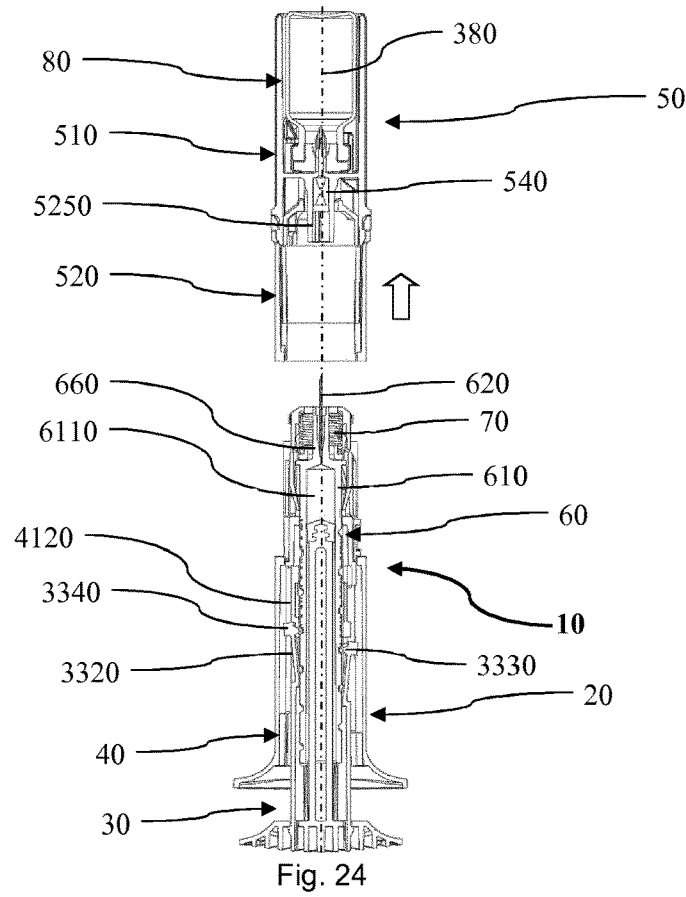
FIG. 24 shows a cross sectional view of the medical delivery device of FIG. 23.

In FIG. 23 and FIG. 24 the medical delivery device 10 is shown after dosing wherein the dosing activator 50 together with the vial 80 is removed. As indicated by the arrows, once the dosage is set as described above the dosing activator 50 is upwardly or proximally pulled off the housing 20 by the user. Thereby, the male coupling structure 660 of the dosage member 60 disengages the female coupling structure 5250 of the dosing activator 50. Also the needle seal 540 being connected to the rest of the dosing activator 50 is pulled off the needle 620 such that the needle 620 is exposed.

When the dosing activator 50 being pulled off, the medical delivery device 10 is switched from the dosing status into a delivery status ready to inject the liquid or medicament. In order to be switched into the delivery status, the switch activator 40 is rotated to a certain extent around the axis 380 relative to the housing 20 and relative to the rod element 30. Thereby, the slanting surfaces 4120 limiting the recesses 4110 of the switch activator 40 act on the release humps 3340 of the rod element 30. Due to the inclined orientation the slanting surfaces 4120 push the release humps 3340 tangentially in an outward direction. Thereby, the arm sections 3320 are outwardly bent and the pins 3330 are disengaged from the thread 650 of the dosage member 60. In the delivery status shown in FIG. 23 and FIG. 24, the pins 3330 are completely disengaged from the thread 650. Like this, an axial movement of the rod element 30 caused by an axial force is no longer prevented by the pins 3330.

Figure 25:
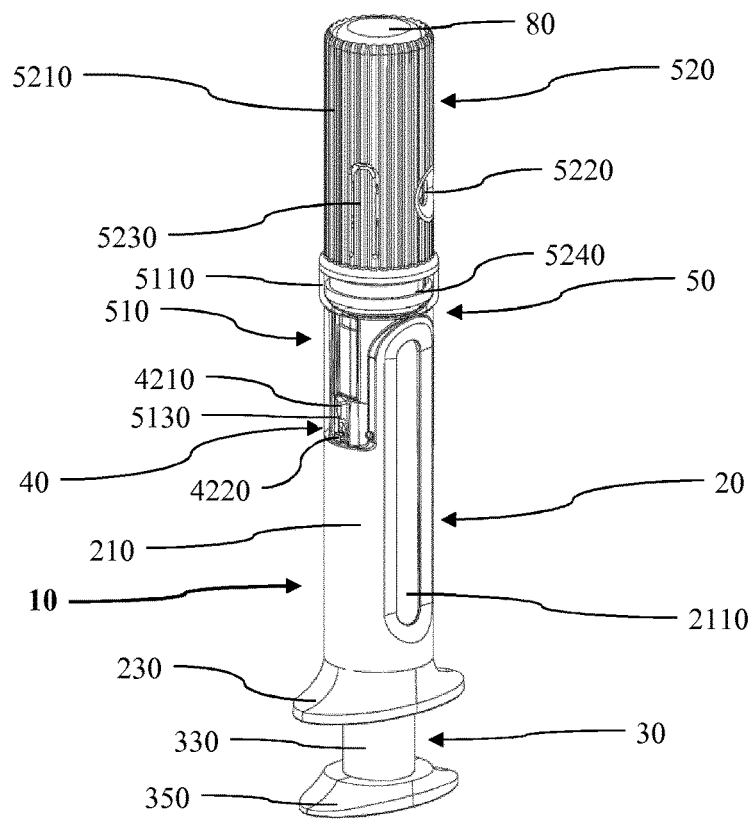
FIG. 25 shows a perspective view of the medical delivery device of FIG. 16 in the beginning of switching from the dosing status to the delivery status by removing the dosing activator.
Figure 26:
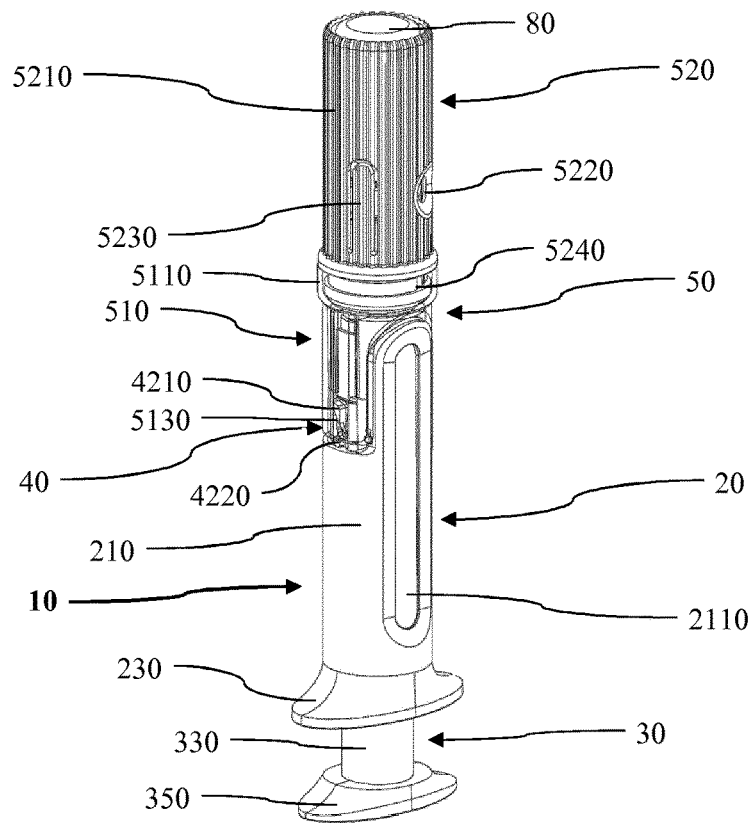
FIG. 26 shows a perspective view of the medical delivery device of FIG. 16 while switching from the dosing status to the delivery status by removing the dosing activator.
Figure 27:
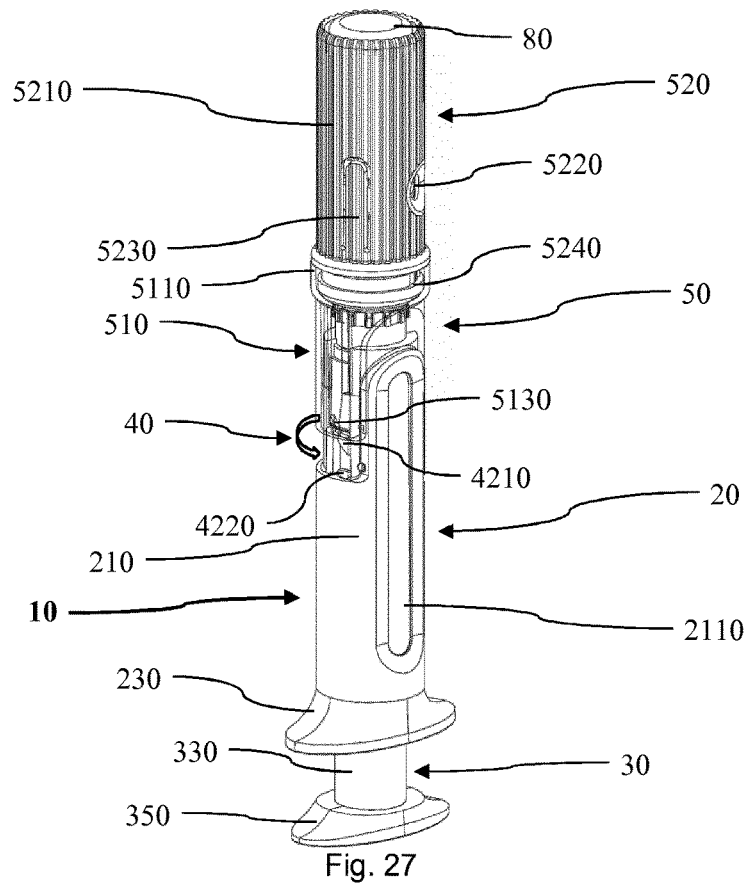
FIG. 27 shows a perspective view of the medical delivery device of FIG. 16 after switching from the dosing status to the delivery status by removing the dosing activator.

As shown in FIG. 25, FIG. 26 and FIG. 27, the mentioned rotation of the switch activator 40 is automatically induced when pulling off the dosing activator 50 from the housing 20. In these Figs. the sleeve unit 510 of the dosing activator 50 is transparently displayed in order to allow seeing how some parts below it interact. The sleeve unit 510 is equipped with the two first ramps 5130 and the switch activator 40 with associated two second ramps 4110. In particular, as can be seen in FIG. 25, in the dosing status of the medical delivery device 10 the first ramp 5130 of the sleeve unit 510 is below the second ramp 4210 of the switch activator 40. The first and second ramps 5130, 4210 have inclined sliding surfaces which are oriented towards each other. Thereby, the inclined sliding surface of the second ramps 4210 of the switch activator 40 is downwardly oriented and the inclined first ramp 5130 of the sleeve unit 510 is upwardly oriented.

As shown in FIG. 26, when the dosing activator 50 together with the sleeve unit 510 is upwardly moved relative to the body 20 the inclined sliding surfaces of the first ramp 5130 contacts the inclined sliding surface of the second ramp 4210. Like this, the second ramp 4210 of the switch activator 40 slides along the ramp 5130 of the sleeve unit 510 such that the switch activator 40 is rotated in a counter clockwise direction.

FIG. 27 shows that in the delivery status the switch activator 40 is rotated far enough such that the first ramp 5130 can axially pass the second ramp 4210. In this manner, the dosing activator 50 can be pulled off and removed from the housing 20. At the same time the medical delivery device 10 is switched from its dosing status to its delivery status. In order that an unintended back rotation of the switch activator 40 is prevented, the backup member 4220 of the switch activator 40 snaps behind a corresponding element of the housing 20. Like this, the medical delivery device 10 can be safely kept in its delivery status.

When rotating the switch activator 40 the lockout member 90 is ready to be activated by rotation of the switch activator relative 40 to the lockout member 90. In particular, the second ramp 4210 interacts with corresponding protrusion on the lockout member. Thereby, an indicator sign of the lockout member 90 is visible showing that dosing is finished. Furthermore, by activating the lockout member 90 and thereby the release mechanism, the spring 70 is prepared to move the housing 20 after delivery as shown below.

Figure 28:
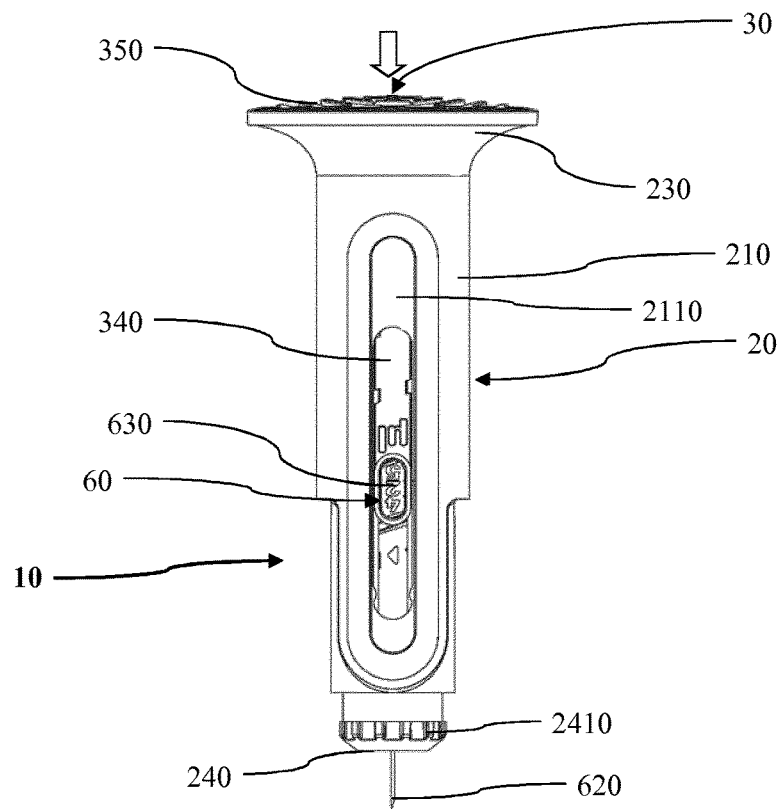
FIG. 28 shows a front view of an injection device of the medical delivery device of FIG. 16 in the delivery status after delivery.
Figure 29:
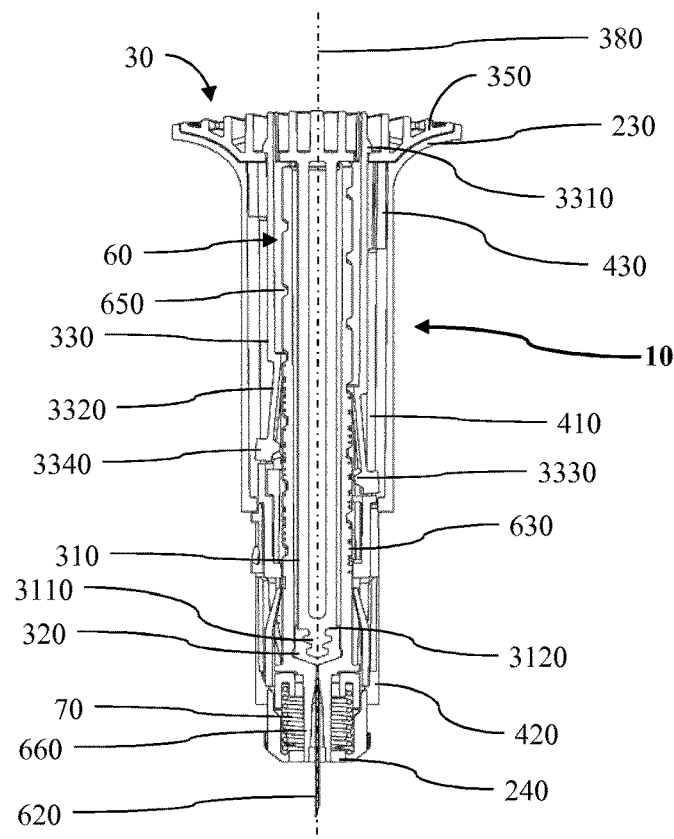
FIG. 29 shows a cross sectional view of the injection device of FIG. 28.

In FIG. 28 and FIG. 29 the injection device is shown in the delivery status of the medical delivery device 10 prior injection. Compared to the preceding Figs., in FIG. 28 and FIG. 29 the injection device is turned upside down by 180°.

As indicated by the arrow in FIG. 28 the rod element 30 is moved downwardly. More particularly, for injecting the liquid or medicament a manual axial force is applied on the distal end of the push cone 350 of the rod element 30. For example, such axial force can be provided by a thumb of a hand of the user wherein the housing 20 is held by the user. During injection, the axial force is transmitted from the rod element 30 to the stopper 320 thereby pressing it into the dosage chamber 6110 and the liquid or medicament is supplied out of the delivery needle 620. After injection, as shown in FIG. 29, the volume of the dosage chamber 6110 is minimized such that the liquid is essentially completely delivered.

Figure 30:
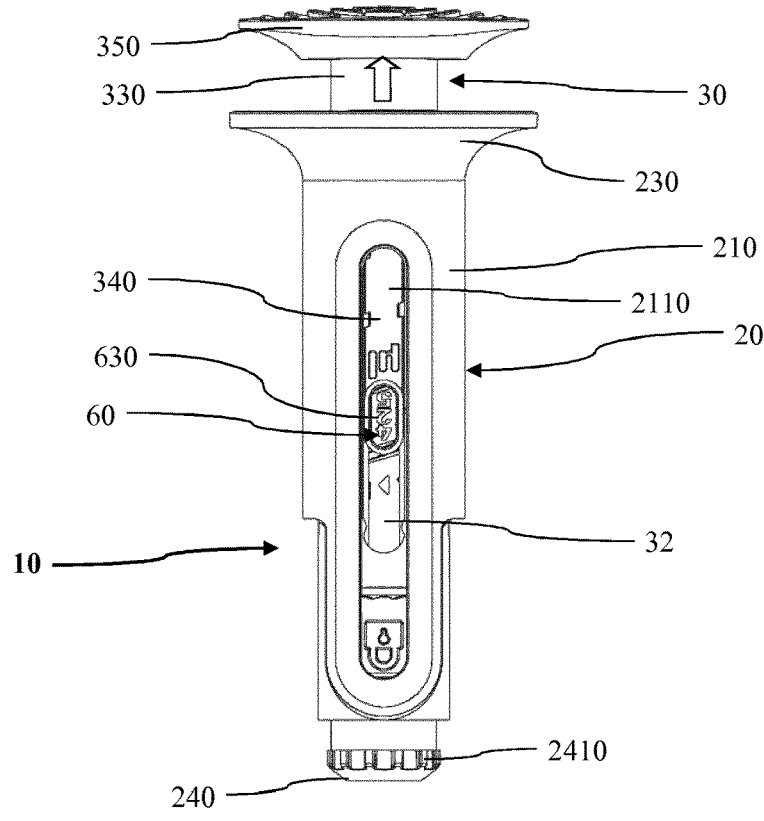
FIG. 30 shows a front view of the injection device of the medical delivery device of FIG. 16 after delivery when a needle is covered and protected.
Figure 31:
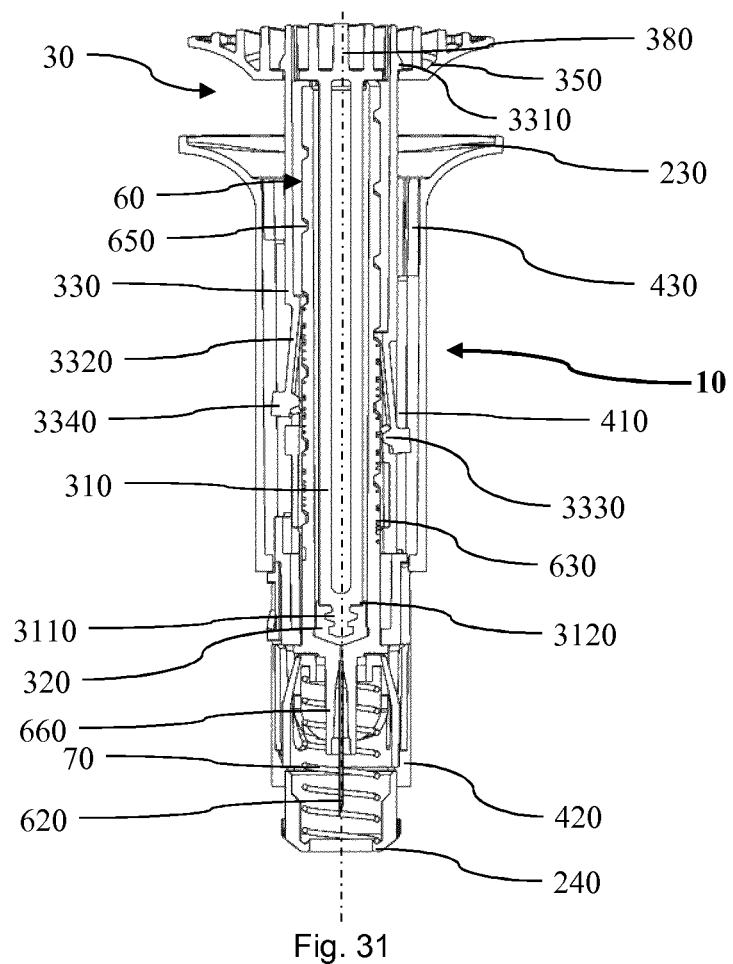
FIG. 31 shows a cross sectional view of the injection device of FIG. 30.

FIG. 30 and FIG. 31 show the injection device after delivery with its needle 620 protected. In particular, the spring force of the spring 70 initially being pre-stressed between the housing 20 as cage body and the lockout member 90 axially moves the housing 20 in relation to the other parts of the injection device and particularly also in relation to the needle 620. Like this, the needle 620 is retracted and therefore completely covered by the housing 20 which can prevent injuries by the needle 620 after injection. In addition, the lockout member 90 informs the user that the injection has been completed and the injection device cannot be used anymore.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The present disclosure comprises further the following embodiments of medical delivery devices, the following embodiments adapters and the following embodiments of methods:

Embodiment 1 is a medical delivery device, comprising a rod element having a stem with a longitudinal axis, a distal end, a proximal end and a stopper mounted to a head portion of the proximal end of the stem, a dosage member comprising a delivery orifice and a chamber body with a distal end, a proximal end and a hollow interior, wherein the stem of the rod element extends into the interior of the chamber body of the dosage member the delivery orifice is arranged adjacent to the stopper of the rod element and the stopper tightly fits into the interior of the chamber body. The head portion of the stem has plural bulges and the stopper has a corresponding interior, wherein the complete head portion of the stem is fitted into the interior of the stopper.

Embodiment 2 is a medical delivery device according to embodiment 1, wherein, in a dosing status of the medical delivery device, the rod element is movable along its longitudinal axis relative to the delivery orifice of the dosage member, such that a dosage chamber is formed in the interior of the chamber body of the dosage member between the stem of the rod element and the delivery orifice which dosage chamber increases when the rod element moves away from the delivery orifice.

Embodiment 3 is a medical delivery device according to embodiment 1 or 2, wherein the stopper is made of an elastic material.

Embodiment 4 is a medical delivery device according to any one of embodiments 1 to 3, wherein the plural bulges of the head portion of the stem are convex.

Embodiment 5 is a medical delivery device according to any one of embodiments 1 to 4, wherein neighbouring of the plural bulges of the head portion of the stem of the rod element are separated by a concave intermediate section.

Embodiment 6 is a medical delivery device according to any one of embodiments 1 to 5, wherein the stem of the rod element comprises an abutting face from which the head portion extends.

Embodiment 7 is a medical delivery device according to embodiment 6, wherein the stopper axially abuts the abutting face of the stem of the rod element.

Embodiment 8 is a medical delivery device according to any one of embodiments 1 to 7, wherein the head portion of the stem of the rod element has a reduced diameter compared to the rest of the stem.

Embodiment 9 is a medical delivery device according to any one of embodiments 1 to 8, wherein the stem of the rod element is rotational symmetric.

Embodiment 10 is an adapter for connecting a container to a delivery device having a delivery orifice, comprising a mounting structure arranged to connect the adapter to and disconnect the adapter from the delivery device, and a container seat for holding a container in a predefined position relative to a tip of the delivery orifice of the delivery device. When a container is arranged in the container seat of the adapter and the mounting structure of the adapter is connected to the delivery device, an open duct is formed between an interior of the container and an interior of the delivery orifice of the delivery device. The container seat of the adapter comprises a spike which penetrates a cap of an opening of the container when the container is arranged in the container seat of the adapter.

Embodiment 11 is an adapter according to embodiment 1, wherein the spike of the container seat extends in the interior of the container seat.

Embodiment 12 is an adapter according to embodiment 10 or 11, wherein the spike of the container seat comprises a tip.

Embodiment 13 is an adapter according to embodiment 12, wherein the spike of the container seat comprises a conduit which runs from the tip longitudinally through the spike.

Embodiment 14 is an adapter according to any one of embodiments 10 to 13, further comprising a delivery orifice seal which seals the delivery orifice of the delivery device when the mounting structure of the adapter is connected to the delivery device.

Embodiment 15 is an adapter according to embodiment 14, comprising a seal holder in which the delivery orifice seal is tightly arranged.

Embodiment 16 is an adapter according to embodiment 14 or 15, wherein the delivery orifice seal comprises a passage through which the delivery orifice extends when the mounting structure of the adapter is connected to the delivery device.

Embodiment 17 is an adapter according to embodiment 13 and any one of embodiments 15 to 16, wherein the delivery orifice of the delivery device extends into the conduit of the spike of the container seat when the mounting structure of the adapter is connected to the delivery device.

Embodiment 18 is an adapter according to embodiment 17, wherein the delivery orifice seal tightly abuts the spike of the container seat at a side of the spike where the conduit ends opposite to the tip.

Embodiment 19 is an adapter according to any one of embodiments 14 to 18, wherein the delivery orifice seal is shaped as a plug.

Embodiment 20 is an adapter according to any one of embodiments 14 to 19, wherein the delivery orifice seal is made of silicone.

Embodiment 21 is a method of delivering a liquid to a patient, comprising obtaining a liquid in a container, a delivery device with a delivery orifice and an adapter according to any one of embodiments 10 to 20, arranging the container in a container seat of the adapter, withdrawing a liquid from the container into the delivery device via its delivery orifice while the mounting structure of the adapter is connected to the delivery device and the container is arranged in the container seat of the adapter, decoupling the adapter from the delivery device, and providing the liquid out of the delivery device via the delivery orifice.

The invention claimed is:

1. A medical delivery device, comprising:
  a rod element having a stem with a longitudinal axis, a first thread arrangement, a distal end and a proximal end; and
  a dosage member comprising a delivery orifice and a chamber body with a distal end, a proximal end and a hollow interior, wherein the stem of the rod element extends into the interior of the chamber body of the dosage member and the delivery orifice is arranged adjacent to the proximal end of the stem of the rod element,
  wherein, in a dosing status of the medical delivery device, the rod element is movable along its longitudinal axis relative to the delivery orifice of the dosage member by the first thread arrangement of the rod element and a second thread arrangement travelling along each other, wherein a dosage chamber is formed in the interior of the chamber body of the dosage member between the stem of the rod element and the delivery orifice which dosage chamber increases when the rod element moves away from the delivery orifice, and the dosage member comprises the second thread arrangement, wherein, in the dosing status of the medical delivery device, the first thread arrangement of the rod element engages the second thread arrangement of the dosage member.

2. The medical delivery device according to claim 1, wherein the second thread arrangement is arranged at an outer surface of the chamber body of the dosage member, the first thread arrangement of the rod element comprises an arm section extending beneath the stem and, in the dosing status of the medical delivery device, the first thread arrangement of the rod element engages the second thread arrangement of the dosage member via the arm section.

3. The medical delivery device according to claim 1, wherein the first thread arrangement of the rod element is a pin arrangement with at least one pin, the second thread arrangement of the dosage member comprises a thread and the first thread arrangement of the rod element engages the second thread arrangement of the dosage member by the at least one pin of the pin arrangement of the rod element being located in the thread of the second thread arrangement of the dosage member.

4. The medical delivery device according to claim 1, wherein, in the dosing status of the medical delivery device, the dosage member is rotatable in relation to the rod element such that the first thread arrangement of the rod element and the second thread arrangement of the dosage member travel along each other and the rod element moves along the longitudinal axis of its stem relative to the delivery orifice.

5. The medical delivery device according to claim 4, comprising a dosing activator, wherein the dosage member has a first coupling structure, the dosing activator has a second coupling structure corresponding to the first coupling structure and the dosing activator is torque resistantly connected to the dosage member when the second coupling structure is mounted to the first coupling structure.

6. The medical delivery device according to claim 5, wherein the dosing activator comprises a container seat for holding a container in a predefined position.

7. The medical delivery device according to claim 6, wherein the delivery orifice connects the container seat of the dosing activator with the dosage chamber of the dosage member such that, when a container is arranged in the container seat of the dosing activator, an open duct is formed between an interior of the container and the dosage chamber of the dosage member.

8. The medical delivery device according to claim 6, wherein the container seat of the dosing activator comprises a spike which penetrates a cap of an opening of a container when the container is arranged in the container seat the dosing activator.

9. The medical delivery device according to claim 5, wherein the dosing activator comprises an orifice seal which seals the delivery orifice of the dosage member when the second coupling structure of the dosing activator is mounted to the first coupling structure of the dosage member.

10. The medical delivery device according to claim 6, wherein a fluid is transferred from a container through the delivery orifice to the dosage chamber when the container is arranged in the container seat of the dosing activator and the rod element and the dosage member are rotated in a first direction relative to each other.

11. The medical delivery device according to claim 10, wherein the fluid is transferred from the dosage chamber through the delivery orifice to the container when the container is arranged in the container seat of the dosing activator and the rod element and the dosage member are rotated in a second direction opposite to the first direction relative to each other.

12. The medical delivery device according to claim 1, comprising a switching mechanism for changing the medical delivery device from the dosing status to a delivery status, wherein in the dosing status of the medical delivery device, moving the rod element along its longitudinal axis by applying an axial force to the rod element is prevented, and in the delivery status of the medical delivery device, the rod element is movable along its longitudinal axis relative to the delivery orifice by applying an axial force to the rod element, and moving the rod element along its longitudinal axis by rotating a dial shell around the stem of the rod element is prevented.

13. The medical delivery device according to claim 12, wherein the switching mechanism comprises a disengaging structure which disengages the first thread arrangement of the rod element from the second thread arrangement of the dosage member upon changing the medical delivery device from the dosing status to the delivery status.

14. The medical delivery device according to claim 12, wherein the switching mechanism comprises a release shell with a recess, in the dosing status of the medical delivery device, the release shell holds an arm section of the rod element in a pre-tensioned position such that the first thread arrangement of the rod element engages the second thread arrangement of the dosage member via the arm section, upon switching the medical delivery device from the dosing status to the delivery status, the release shell of the switching mechanism is moved relative to the arm section of the rod element, and in the delivery status of the medical delivery device, the arm section of the rod element is positioned in the recess of the release shell such that the first thread arrangement of the rod element is disengaged from the second thread arrangement of the dosage member.

15. The medical delivery device according to claim 1, comprising a counter coupled to the rod element such that the counter indicates the dosage volume formed by the rod element when being moved along its longitudinal axis relative to the delivery orifice by rotating the dosage member and the rod element relative to each other.

* * * * *